US006001608A

United States Patent [19]
Lambowitz et al.

[11] Patent Number: 6,001,608
[45] Date of Patent: Dec. 14, 1999

[54] METHODS OF MAKING AN RNP PARTICLE HAVING NUCLEOTIDE INTEGRASE ACTIVITY

[75] Inventors: Alan M. Lambowitz; Georg Mohr; Roland Saldanha; Manabu Matsuura, all of Austin, Tex.; Clifford James Beall, Columbus, Ohio; Jiam Yang, Dallas, Tex.; Steven Zimmerly, Calgary, Canada; Huatao Guo, Austin, Tex.

[73] Assignee: The Ohio State Research Foundation, Columbus, Ohio

[21] Appl. No.: 09/085,603

[22] Filed: May 27, 1998

Related U.S. Application Data

[63] Continuation-in-part of application No. 08/752,238, Nov. 19, 1996, Pat. No. 5,804,418.

[51] Int. Cl.$^6$ .............................. C12P 19/34; C12P 21/06; C12N 9/12; C07H 21/04
[52] U.S. Cl. ........................ 435/91.1; 435/69.1; 435/194; 536/23.2; 536/23.4; 536/24.1
[58] Field of Search ................................... 435/69.1, 194, 435/91.1; 536/23.2, 23.4, 24.1

[56] References Cited

U.S. PATENT DOCUMENTS

| | | | |
|---|---|---|---|
| 5,498,531 | 3/1996 | Jarrell | 435/91.31 |
| 5,698,421 | 12/1997 | Lambowitz et al. | 435/91.1 |
| 5,804,418 | 9/1998 | Lambowitz et al. | 435/69.1 |

OTHER PUBLICATIONS

"Group I and group II introns" by Saldanha, et al., *The FASEB Journal*, vol. 7, Jan., 1993, pp. 15–24.
"Group II Intron Mobility Occurs to Target DNA–Primed Reverse Transcription" by Zimmerly, et al., *Cell*, vol. 82, Aug. 25, 1995, pp. 545–554.
"An Expanding Universe of Introns" by Belfort, *Science*, vol. 262, Nov. 12, 1993, pp. 1009–1010.
"Integration of Group II Intron b11 into a Foreign RNA by Reversal of the Self–Splicing Reaction in Vitro", by Morl and Schmelzer, *Cell*, vol. 60, Feb. 23, 1990, pp. 629–636.
"A Group II Intron RNA is a Catalytic Component of a DNA Endonuclease Involved in Intron Mobility", by Zimmerly, et al., *Cell*, vol. 83, Nov. 17, 1995, pp. 1–10.
"RNA enzymes (ribozymes) as antiviral therapeutic agents" by Rossi and Sarver, *Tibtech*, vol. 8, Jul., 1990, pp. 179–183.
"Mobile Group II Introns of Yeast Mitochondrial DNA Are Novel Site–Specific Retroelements" by Moran, et al., *Molecular and Cellular Biology*, vol. 15, No. 5, May 1995, pp. 2828–2838.
"Evolutionary relationships among group II intorn–encoded proteins and identification of a conserved domain that may be related to maturase function" by Mohr, et al., *Nucleic Acids Research*, vol. 21, No. 22, 1993, pp. 4991–4997.
"Reverse Transcriptase Activity Associated with Maturase–Encoding Group II Introns in Yeast Nitochondria" by Kennell, et al., *Cell*, vol. 73, Apr. 9, 1993, pp. 133–146.

"Introns as Mobile Genetic Elements" by Lambowitz, et al., *Annual Reviews Biochem.*, vol. 62, 1993, pp. 587–622.
"A bacterial group II intron encoding reverse transcriptase, maturase, and DNA endonuclease activities: biochemical demonstration of maturase activity and insertion of new genetic information within the intron" Matsuura, et al., *Genes & Development*, vol. 11, 1997, pp. 2910–2924.
"Group II intron endonucleases use both RNA and protein subuints for recognition of specific sequences in double–stranded DNA" by Guo, et al., *The EMBO Journal*, vol. 16, No. 22, 1997, pp. 6835–6848.
"Efficient integration of an intron RNA into double–stranded DNA by reversing splicing" by Yang, et al., *Nature*, vol. 381, No. 23, May 1996, pp. 332–335.
"Mobility of Yeast Mitochondrial Group II Introns: Engineering a New Site Specifically and Retrohoming via Full Reverse Splicing" by Eskes, et al., *Cell*, vol. 88, Mar. 21, 1997, pp. 865–874.
"Splicing of a Group II Intron Involved in the Conjugative Transfer of pRS01 in Lactococci" by Mills, et al., *Journal of Bacteriology*, vol. 178, No. 12, Jun. 1996, pp. 3531–3538.
"Splicing of a group II intron in a functional transfer gene of *Lactococcus lactis*" by Shearman, et al., *Molecular Microbiology*, vol. 21, 1996, pp. 45–53.

(List continued on next page.)

*Primary Examiner*—George C. Elliott
*Assistant Examiner*—Andrew Wang
*Attorney, Agent, or Firm*—Calfee, Halter & Griswold LLP

[57] ABSTRACT

Methods for preparing nucleotide integrases are provided. The nucleotide integrases are prepared by combining in vitro an excised, group II intron RNA, referred to hereinafter as "exogenous RNA", with a group II intron-encoded protein. The exogenous RNA is prepared by in vitro transcription of a DNA molecule which comprises a group II intron sequence. In one embodiment, the group II intron-encoded protein is made by introducing into a host cell a DNA molecule that comprises at least the open reading frame sequence of a group II intron and then expressing the open reading frame sequence in the host cell. The DNA molecule may comprise the open reading frame sequence operably linked to a promoter, preferably an inducible promoter. Thereafter, the cell is fractionated and the protein is recovered and combined in vitro with the exogenous RNA to provide RNP particles having nucleotide integrase activity. In another embodiment, the DNA molecule comprise a group II intron sequence that encodes both a group II intron RNA as well as a group II intron encoded protein. The DNA molecule is then expressed in the host cell to provide RNP particles that comprise the group II intron-encoded protein bound to the group II intron RNA. Thereafter, the RNP particles comprising the group II intron-encoded protein and the group II intron RNA are isolated from the cell and treated with a nuclease to remove the RNA and to provide the group II-intron encoded protein. The group II intron-encoded protein is then combined in vitro with the exogenous RNA to provide RNP particles having nucleotide integrase activity.

17 Claims, 9 Drawing Sheets

OTHER PUBLICATIONS

"Targeted DNA cleavage and insertion by group II introns" by Guo, et al., *RNA '97, The second annual meeting of the RNA society*, May 27–Jun. 1, 1997, p. 262.

"A bacterial group II intorn encoding reverse transcriptase, maturase, and DNA endonuclease activities" by Matsuura, et al., *RNA '97, The second annual meeting of the RNA society*, May 27–Jun. 1, 1997, p. 369.

"Novel mechanisms for site–specific DNA cleavage and insertion involving group II intron catalytic RNAs" by Lambowitz, Functional Genomics Conference, Newport, Rhode Island, Nov. 2–5, 1997.

"Group II introns as site–specific retroelements", by Guo, et al., Keystone Symposia on Molecular and Cellular Biology: Transposition and Site–Specific Recombination, Santa Fe, New Mexico, Mar. 1–7, 1997.

"Group II intron mobility and evolution" by Zimmerly, et al., Keystone Symposia on Molecular and Cellular Biology: Posttranscriptional RNA Processing, Hilton Head, South Carolina, Mach 11–17, 1996.

"Retrotransposition of group II introns" by Zimmerly, et al., Keystone Symposia on Molecular and Cellular Biology: Viral Genome Replication, Tamarron, Colorado, Mar. 1–7, 1996.

"Mitochondrial plasmid and group II intron reverse transcription" by Lambowitz, et al., Keystone Symposia on Molecular and Cellular Biology: Viral Genome Replication, Tamorron, Colorado, Mar. 1–7, 1996.

"Homing of a Group II Intron from *Lactococcus lactis* subsp. *lactis* ML3" by Mills, et al., *Journal of Bacteriology*, Oct. 1997, vol. 179, No. 19, pp. 6107–6111.

Fig. 4

```
         10         20         30         40         50         60         70         80         90
aagcttAGAG AAAAATAATG CGGTGCTTGG TCATCACCTC ATCCAATCAT TTTCTCCTGA TGACAATCTA ACTCCTGAAC AAATTCATGA 100        110        120        130        140        150        160        170        180
AATAGGTCGT CAAACCATAT TAGAATTTAC AGGTGGCGAA TATGAATTTG TGATTGCAAC CCACGTCGAT CGTGAACACA TCCATAACGT 190        200        210        220        230        240        250        260        270
GCGCCCAGAT AGGGTGTTAA GTCAAGTAGT TTAAGGTACT ACTCTGTAAG ATAACACAGA AAACAGCCAA CCTAACCGAA AAGCGAAAGC 280        290        300        310        320        330        340        350        360
TGATACGGGA ACAGAGCACG GTTGGAAAGC GATGAGTTAC CTAAAGACAA TCGGGTACGA CTGAGTCGCA ATGTTAATCA GATATAAGGT 370        380        390        400        410        420        430        440        450
ATAAGTTGTG TTTACTGAAC GCAAGTTTCT AATTTCGGTT ATGTGTCGAT AGAGGAAAGT GTCTGAAACC TCTAGTACAA AGAAAGGTAA 460        470        480        490        500        510        520        530        540
GTTATGGTTG TGGACTTATC TGTTATCACC ACATTTGTAC AATCTGTAGG AGAACCTATG GAACGAAAC GAAAGCGATG CCGAGAATCT 550        560        570        580        590        600        610        620        630
GAATTTACCA AGACTTAACA CTAACTGGGG ATACCCTAAA CAAGAATGCC TAATAGAAAG GAGGAAAAAG GCTATAGCAC TAGAGCTTGA 640        650        660        670        680        690        700        710        720
AAATCTTGCA AGGGTACGGA GTACTCGTAG TAGTCTGAGA AGGGTAACGC CCTTTACATG GCAAGGGGT ACAGTTATTG TGTACTAAAA 730        740        750        760        770        780        790        800        810
TTAAAAATTG ATTAGGGAGG AAAACCTCAA AATGAAACCA ACAATGGCAA TTTTAGAAAG AATCAGTAAA AATTCACAAG AAAATATAGA
                                             M  K  P  T  M  A  I  L  E  R  I  S  K  N  S  Q  E  N  I  D 820        830        840        850        860        870        880        890        900
CGAAGTTTTT ACAAGACTTT ATCGTTATCT TTTACGTCCA GATATTTATT ACGTGGCGTA TCAAAATTTA TATTCCAATA AAGGAGCTTC
 E  V  F  T  R  L  Y  R  Y  L  L  R  P  D  I  Y  Y  V  A  Y  Q  N  L  Y  S  N  K  G  A  S 910        920        930        940        950        960        970        980        990
CACAAAAGGA ATATTAGATG ATACAGCGGA TGGCTTTAGT GAAGAAAAA TAAAAAAGAT TATTCAATCT TTAAAAGACG GAACTTACTA
 T  K  G  I  L  D  D  T  A  D  G  F  S  E  E  K  I  K  K  I  Q  S  L  K  D  G  T  Y  Y 1000       1010       1020       1030       1040       1050       1060       1070       1080
TCCTCAACCT GTACGAAGAA TGTATATTGC AAAAAAGAAT TCTAAAAAGA TGAGACCTTT AGGAATTCCA ACTTTACAG ATAAATTGAT
 P  Q  P  V  R  R  M  Y  I  A  K  K  N  S  K  K  M  R  P  L  G  I  P  T  F  T  D  K  L  I 1090       1100       1110       1120       1130       1140       1150       1160       1170
CCAAGAAGCT GTGAGAATAA TTCTTGAATC TATCTATGAA CCGGTATTCG AAGATGTGTC TCACGGTTTT AGACCTCAAC GAAGCTGTCA
 Q  E  A  V  R  I  I  L  E  S  I  Y  E  P  V  F  E  D  V  S  H  G  F  R  P  Q  R  S  C  H 1180       1190       1200       1210       1220       1230       1240       1250       1260
CACAGCTTTG AAAACAATCA AAAGAGAGTT TGGCGGCGCA AGATGGTTTG TGGAGGGAGA TATAAAAGGC TGCTTCGATA ATATAGACCA
 T  A  L  K  T  I  K  R  E  F  G  G  A  R  W  F  V  E  G  D  I  K  G  C  F  D  N  I  D  H 1270       1280       1290       1300       1310       1320       1330       1340       1350
CGTTACACTC ATTGGACTCA TCAATCTTAA AATCAAAGAT ATGAAAATGA GCCAATTGAT TTATAAATTT CTAAAAGCAG GTTATCTGGA
 V  T  L  I  G  L  I  N  L  K  I  K  D  M  K  M  S  Q  L  I  Y  K  F  L  K  A  G  Y  L  E 1360       1370       1380       1390       1400       1410       1420       1430       1440
AAACTGGCAG TATCACAAAA CTTACAGCGG AACACCTCAA GGTGGAATTC TATCTCCTCT TTTGGCCAAC ATCTATCTTC ATGAATTGGA
 N  W  Q  Y  H  K  T  Y  S  G  T  P  Q  G  G  I  L  S  P  L  A  N  I  Y  L  H  E  L  D 1450       1460       1470       1480       1490       1500       1510       1520       1530
TAAGTTTGTT TTACAACTCA AAATGAAGTT TGACCGAGAA AGTCCAGAAA GAATAACACC TGAATATCGG GAACTTCACA ATGAGATAAA
 K  F  V  L  Q  L  K  M  E  F  D  R  E  S  P  E  R  I  T  P  E  Y  R  E  L  H  N  E  I  K
```

Fig. 4 (con't)

```
          1540       1550       1560       1570       1580       1590       1600       1610       1620
     AAGAATTTCT CACCGTCTCA AGAAGTTGGA GGGTGAAGAA AAAGCTAAAG TTCTTTTAGA ATATCAAGAA AAACGTAAAA GATTACCCAC
       R  I  S   H  R  L     K  L  E    G  E  E    K  A  V    L  L  E    Y  Q  E    K  R  K     L  P  T 1630       1640       1650       1660       1670       1680       1690       1700       1710
     ACTCCCCTGT ACCTCACAGA CAAATAAAGT ATTGAAATAC GTCCGGTATG CGGACGACTT CATTATCTCT GTTAAAGGAA GCAAAGAGGA
       L  P  C    T  S  Q  T    N  K  V    L  K  Y    V  R  Y  A    D  D  F    I  I  S    V  K  G     K  E  D 1720       1730       1740       1750       1760       1770       1780       1790       1800
     CTGTCAATGG ATAAAAGAAC AATTAAAACT TTTTATTCAT AACAAGCTAA AAATGGAATT GAGTGAAGAA AAAACACTCA TCACACATAG
       C  Q  W    I  K  E  Q    L  K  L    F  I  H    N  K  L    K  M  E  L    S  E  E    K  T  L  I    T  H  S 1810       1820       1830       1840       1850       1860       1870       1880       1890
     CAGTCAACCC GCTCGTTTTC TGGGATATGA TATACGAGTA AGGAGAAGTG GAACGATAAA ACGATCTGGT AAAGTCAAAA AGAGAACACT
       S  Q  P    A  R  F  L    G  Y  D    I  R  V    R  R  S  G    T  I  K     R  S  G    K  V  K  K    R  T  L 1900       1910       1920       1930       1940       1950       1960       1970       1980
     CAATGGGAGT GTAGAACTCC TTATTCCTCT TCAAGACAAA ATTCGTCAAT TTATTTTTGA CAAGAAAATA GCTATCCAAA AGAAAGATAG
       N  G  S    V  E  L  L    I  P  L    Q  D  K    I  R  Q  F    I  F  D    K  K  I    A  I  Q  K    K  D  S 1990       2000       2010       2020       2030       2040       2050       2060       2070
     CTCATGGTTT CCAGTTCACA GGAAATATCT TATTCGTTCA ACAGACTTAG AAATCATCAC AATTTATAAT TCTGAATTAA GAGGGATTTG
       S  W  F    P  V  H  R    K  Y  L    I  R  S    T  D  L  E    I  I  T    I  Y  N    S  E  L  R    G  I  C 2080       2090       2100       2110       2120       2130       2140       2150       2160
     TAATTACTAC GGTCTAGCAA GTAATTTTAA CCAGCTCAAT TATTTTGCTT ATCTTATGGA ATACAGCTGT CTAAAAACGA TAGCCTCCAA
       N  Y  Y    G  L  A  S    N  F  N    Q  L  N    Y  F  A  Y    L  M  E    Y  S  C    L  K  T  I    A  S  K 2170       2180       2190       2200       2210       2220       2230       2240       2250
     ACATAAGGGA ACACTTTCAA AAACCATTTC CATGTTTAAA GATGGAAGTG GTTCGTGGGG CATCCCGTAT GAGATAAAGC AAGGTAAGCA
       H  K  G    T  L  S  K    T  I  S    M  F  K    D  G  S  G    S  W  G    I  P  Y    E  I  K  Q    G  K  Q 2260       2270       2280       2290       2300       2310       2320       2330       2340
     GCGCCGTTAT TTTGCAAATT TTAGTGAATG TAAATCCCCT TATCAATTTA CGGATGAGAT AAGTCAAGCT CCTGTATTGT ATGGCTATGC
       R  R  Y    F  A  N  F    S  E  C    K  S  P    Y  Q  F  T    D  E  I    S  Q  A    P  V  L  Y    G  Y  A 2350       2360       2370       2380       2390       2400       2410       2420       2430
     CCGGAATACT CTTGAAAACA GGTTAAAAGC TAAATGTTGT GAATTATGTG GAACATCTGA TGAAAATACT TCCTATGAAA TTCACCATGT
       R  N  T    L  E  N  R    L  K  A    K  C  C    E  L  C  G    T  S  D    E  N  T    S  Y  E  I    H  H  V 2440       2450       2460       2470       2480       2490       2500       2510       2520
     CAATAAGGTC AAAAATCTTA AAGGCAAAGA AAAATGGGAA ATGGCAATGA TAGCGAAACA ACGTAAAACT CTTGTTGTAT GCTTTCATTG
       N  K  V    K  N  L  K    G  K  E    K  W  E    M  A  M  I    A  K  Q    R  K  T    L  V  V  C    F  H  C 2530       2540       2550       2560       2570       2580       2590       2600       2610
     TCATCGTCAC GTGATTCATA AACACAAGTG AATTTTTACG AACGAACAAT AACAGAGCCG TATACTCCGA GAGGGGTACG TACGGTTCCC
       H  R  H    V  I  H  K    H  K  *

2620       2630       2640       2650       2660       2670       2680       2690       2700
     GAAGAGGGTG GTGCAAACCA GTCACAGTAA TGTGAACAAG GCGGTACCTC CCTACTTCAC|CATATCATTT TTAATTCTAC GAATCTTTAT 2710       2720       2730       2740       2750       2760       2770
     ACTGGCAAAC AATTTGACTG GAAAGTCATT CCTAAAGAGA AAACAAAAAG CGGCAaagct t
```

Fig. 7

A. Wild-type 129 bp dsDNA substrate cgctctagaactagtggatccTTGCAACCCACGTCGATCGTGAACACATCCATAAC|CATATCATTTTTAA
gcgagatcttgatcacctaggAACGTTGGGTGCAGCTAGCACTTGTGTAGGTATTG|GTATAGTAAAAATT TTCTACGAATCTTTATACTGGgaattcgatatcaagcttatcgataccgtcgacctcga 129
AAGATGCTTAGAAATATGACCcttaagctatagttcgaatagctatggcagctggagct B. C-6G 129 bp dsDNA substrate cgctctagaactagtggatccTTGCAACCCACGTCGATCGTGAACACATC<u>G</u>ATAAC|CATATCATTTTTAA
gcgagatcttgatcacctaggAACGTTGGGTGCAGCTAGCACTTGTGTAG<u>C</u>TATTG|GTATAGTAAAAATT TTCTACGAATCTTTATACTGGgaattcgatatcaagcttatcgataccgtcgacctcga 129
AAGATGCTTAGAAATATGACCcttaagctatagttcgaatagctatggcagctggagct UPPER CASE; Lactococcus Ll.ltrB exon sequence
lower case; Vector DNA sequence
vertical line: position 0, exon 1 and exon 2 junction
underlined; mutation in the C-6G dsDNA substrate Fig. 8
DNA Substrate for Endonuclease and Reverse splicing Assay
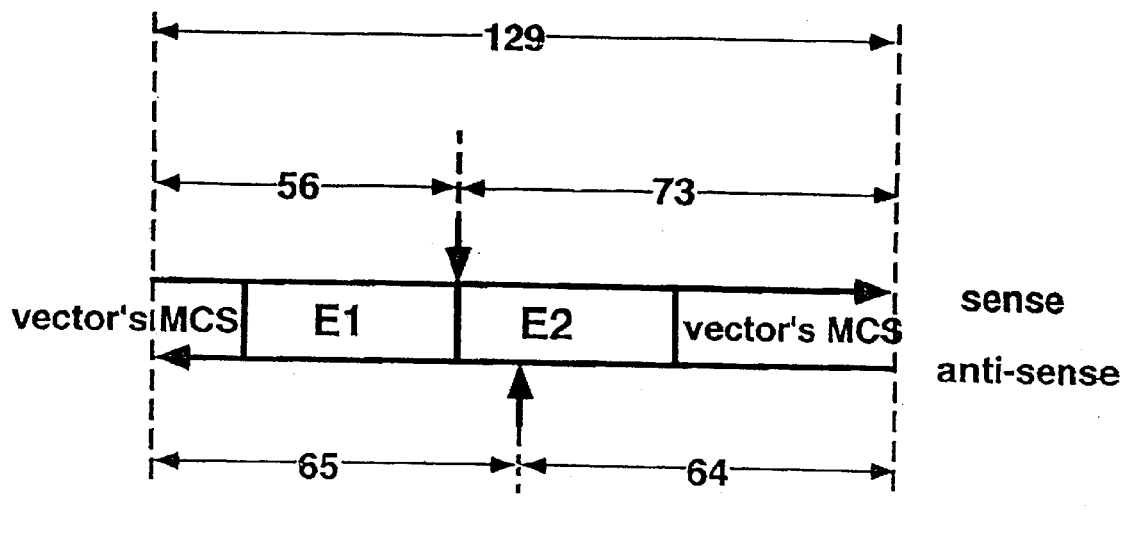
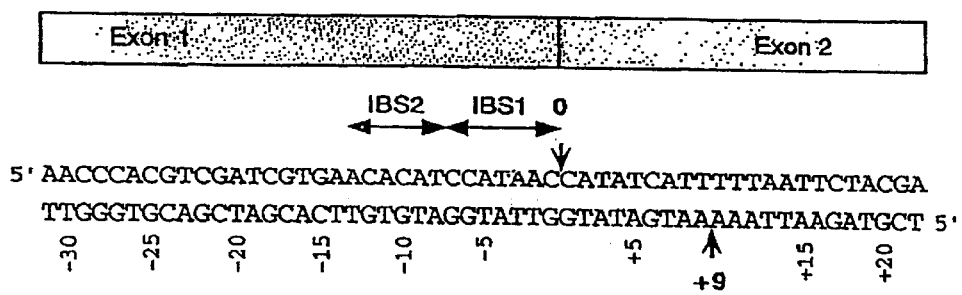
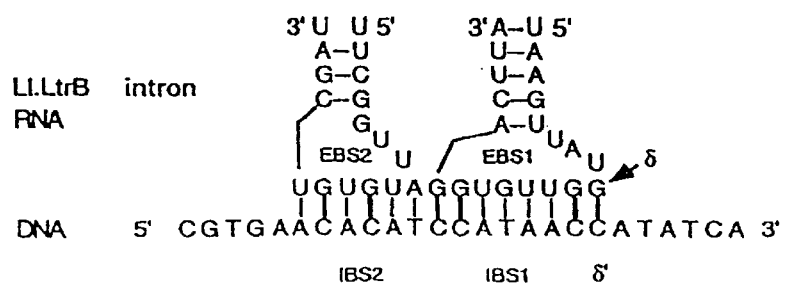

METHODS OF MAKING AN RNP PARTICLE HAVING NUCLEOTIDE INTEGRASE ACTIVITY

CROSS-REFERENCE TO RELATED APPLICATIONS

This application is a continuation-in-part of the, commonly assigned, U.S. patent application Ser. No. 08/752,238, filed Nov. 19, 1996, which issued on Sep. 8, 1998, as U.S. Pat. No. 5,804,418.

The present invention was made with support from National Institutes of Health Grant NO. GM37949. The United States Government has certain rights in the invention.

BACKGROUND

Nucleotide integrases are molecular complexes that are capable of cleaving nucleic acid substrates at specific recognition sites and of concomitantly inserting nucleic acid molecules into the nucleic acid substrate at the cleavage site. Thus, nucleotide integrases are useful tools, particularly for genome mapping, genetic engineering and disrupting the synthesis of gene products. Structurally, nucleotide integrases are ribonucleoprotein (RNP) particles that comprise an excised, group II intron RNA and a group II intron-encoded protein, which is bound to the group II intron RNA.

Conventionally, nucleotide integrases are made by isolating RNP particles that have nucleotide integrase activity from source organisms which comprise a DNA molecule that encodes both the RNA and protein subunits of the nucleotide integrase. In order to obtain nucleotide integrases other than wild type, the source organisms are mutagenized. The mutagenesis is a laborious, multistep process. Moreover, this process yields limited quantities of the nucleotide integrase.

Accordingly, it is desirable to have methods for making nucleotide integrases which are not laborious and which permit the nucleotide integrase to be readily modified from the wild type. Methods which yield at least microgram quantities of substantially pure nucleotide integrases are especially desirable.

SUMMARY OF THE INVENTION

The present invention provides new, improved, and easily manipulable methods for making nucleotide integrases.

In one embodiment, the nucleotide integrase is prepared by introducing a DNA molecule which comprises a group II intron DNA sequence into a host cell. Preferably the DNA molecule further comprises a sequence which encodes a tag that facilitates isolation of RNP particles having nucleotide integrase activity from the host cell. Preferably, the tag sequence is linked to the open reading frame (ORF) sequence of the group II intron DNA. The group II intron DNA sequence is then expressed in the host cell such that RNP particles having nucleotide integrase activity are formed in the cell. Such RNP particles comprise an excised group II intron RNA molecule and a group II intron-encoded protein, both of which are encoded by the introduced DNA molecule. Thereafter, the RNP particles having nucleotide integrase activity are isolated from the cell.

In another embodiment, the nucleotide integrase is prepared by combining in vitro an excised, group II intron RNA, referred to hereinafter as "exogenous RNA", with a group II intron-encoded protein. The exogenous RNA is prepared by in vitro transcription of a DNA molecule which comprises a group II intron sequence. The group II intron-encoded protein is made by introducing into a host cell a DNA molecule that comprises at least the open reading frame sequence of a group II intron and then expressing the open reading frame sequence in the host cell. The DNA molecule may comprise the open reading frame sequence operably linked to a promoter, preferably an inducible promoter. Thereafter, the cell is fractionated and the protein is recovered and combined in vitro with the exogenous RNA to provide RNP particles having nucleotide integrase activity. Alternatively, the DNA molecule may comprise a group II intron sequence that encodes both a group II intron RNA as well as a group II intron encoded protein. The DNA molecule is then expressed in the host cell to provide RNP particles that comprise the group II intron-encoded protein bound to the group II intron RNA. Thereafter, the RNP particles comprising the group II intron-encoded protein and the group II intron RNA are isolated from the cell and treated with a nuclease to remove the RNA and to provide the group II-intron encoded protein. The group II intron-encoded protein is then combined in vitro with the exogenous RNA to provide RNP particles having nucleotide integrase activity.

The present invention also relates to isolated RNP particles having nucleotide integrase activity.

BRIEF DESCRIPTION OF THE DRAWINGS

FIG. 4 shows the nucleotide sequence of the 2.8 kb HindIII fragment that is present in pETLtrAl9 and that includes the L1.ltrB intron DNA sequence and portions of the nucleotide sequence of the flanking exons ltrBE1 and ltrBE2, SEQ. ID. NO. 1., the nucleotide sequence of the LtrA open reading frame, SEQ. ID. NO. 2, and the amino acid sequence of the LtrA protein, SEQ. ID. NO. 3.

FIG. 7A is the sequence of the sense strand of a double-stranded DNA substrate, SEQ. ID. NO. 4, which is cleaved by RNP particles that comprise a wild-type excised, L1.ltrB intron RNA and an LtrA protein.

FIG. 7B is the sequence of the sense strand of a double stranded DNA substrate which is cleaved by RNP particles that comprise an excised L1.ltrB intron RNA having a modified EBS1 sequence and an LtrA protein.

FIG. 8 is a schematic depiction of the substrate which is cleaved by RNP particles comprising the wild-type L1.ltrB intron RNA and the LtrA protein, and shows the IBS1 and IBS2 sequences of the substrate and the cleavage sites of the double-stranded DNA substrate which is cleaved by these RNP particles.

DETAILED DESCRIPTION OF THE INVENTION

Nucleotide Integrases

Functionally, nucleotide integrases are endonucleases that are capable of cleaving nucleic acid substrates at specific recognition sites and of concomitantly inserting nucleic acid molecules into the substrate at the cleavage site. Structurally, nucleotide integrases are ribonucleoprotein (RNP) particles that comprise an excised, group II intron RNA and a group II intron-encoded protein, which is bound to the excised group II intron RNA. "Excised group II intron RNA," as used herein, refers to the RNA that is, or that is derived from, an in vitro or in vivo transcript of the group II intron DNA and that lacks flanking exon sequences at the 5' end and the 3' end of the intron sequence. The excised, group II intron RNA typically has six domains and a characteristic secondary and tertiary structure, which is shown in Saldahana et al., 1993, Federation of the American Society of Experimental Biology Journal, Vol 7 p15–24, which is specifically incorporated herein by reference. Domain IV of the group II intron RNA contains the open reading frame ("ORF") nucleotide sequence which encodes the group II intron encoded protein. The excised group II intron RNA also has two sequences in domain I which are capable of hybridizing with two sequences in the target site of the intended nucleic acid substrate. The first sequence, referred to hereinafter as the "EBS1" sequence, is capable of hybridizing with a sequence, referred to hereinafter as the "IBS1" sequence, which is immediately upstream of the cleavage site in the substrate. The second sequence, referred to hereinafter as the "EBS2" sequence, is capable of hybridizing with a sequence, hereinafter referred to as the "IBS2" sequence, which is upstream of the IBS1 sequence.

The excised group II intron RNA has a wild-type sequence, i.e. a sequence which is identical to the sequence of a group II intron RNA that is found in nature, or the excised group II intron RNA has a modified sequence, i.e. a sequence which is different from the sequence of group II intron RNA molecules that are found in nature. For nucleotide integrases in which the group II intron RNA has a wild-type sequence, the EBS1 sequence typically is complementary to a sequence of about 5–7 nucleotides, hereinafter referred to as the "first set", which is located at the 3' end of the exon that is joined to the 5' end of the intron in the gene. Similarly, the EBS2 sequence of the wild-type group II intron RNA typically is complementary to a sequence of about 5–7 nucleotides in the 5' exon, hereinafter referred to as the "second set", which is upstream, typically immediately upstream, of the first set. Thus, the EBS1 and EBS2 sequences of a wild-type group II intron RNA can usually be predicted by finding sequences in domain I of the intron that are complementary to the first set and second set of nucleotides in the 5' exon.

Figure 1:
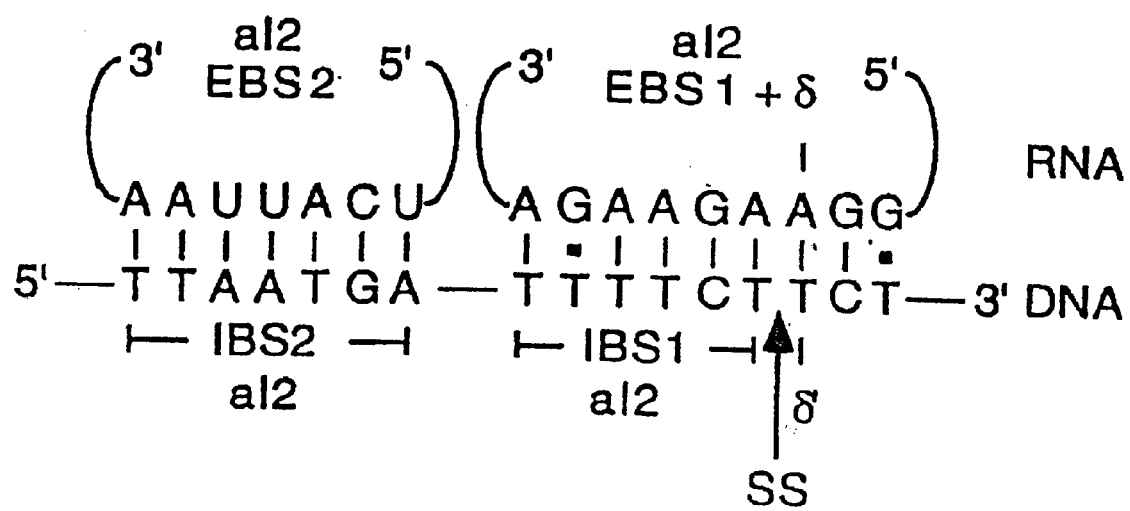
FIG. 1 depicts the interaction at the target site between the EBS1 and EBS2 sequences of the group II intron RNA 2 of the *S. cerevisiae* mitochondrial COX1 gene, hereinafter referred to as the "aI2" RNA, with the IBS1 and IBS2 sequences of a nucleic acid substrate. The cleavage site is represented by an arrow.

In the wild-type group II intron RNA of the *Lactococcus lactis* ltrB gene, hereinafter referred to as the wild-type L1.ltrB intron RNA, EBS1 comprises 7 nucleotides, is located at position 3132–3138 (numbered according to Mills et al., 1996, J. Bact., 178, 3531–3538), and has the sequence GUUGUGG. EBS2 of the wild-type L1.ltrB intron RNA comprises 6 nucleotides, is located at positions 3076–3081 and has the sequence AUGUGU. In the wild-type group II intron RNA 1 of the *S. cerevisiae* mitochondrial COX1 gene, hereinafter referred to as the "wild-type aI1 RNA", EBS1 comprises 6 nucleotides, is located at position 426–431 (numbered according to Bonitz et al., 1980, J. Biol. Chem.: 255, 11927–11941), and has the sequence CGUUGA. EBS2 of the wild-type aI1 RNA comprises 6 nucleotides, is located at positions 376–381 and has the sequence ACAAUU. In the wild-type group II intron RNA 2 of the *S. cerevisiae* mitochondrial COX1 gene, hereinafter referred to as the "wild-type aI2" RNA, EBS1 comprises 6 nucleotides, is located at position 2985–2990 (numbered according to Bonitz et al., 1980, J. Biol. Chem.: 255, 11927–11941) and has the sequence AGAAGA. EBS2 of the wild-type aI2 RNA comprises 7 nucleotides, is located at positions 2935–29410, and has the sequence UCAUUAA. The interaction between EBS1 and EBS2 of the wild-type aI2 RNA with its intended substrate is depicted in FIG. 1.

The excised group II intron RNA may also have a sequence different from a group II intron RNA that is found in nature, and thus be a modified, excised group II intron RNA. Modified excised group II intron RNA molecules, include, for example, group II intron RNA molecules that have nucleotide base changes or additional nucleotides in the internal loop regions of the group II intron RNA, preferably the internal loop region of domain IV and group II intron RNA molecules that have nucleotide base changes in the sequences of EBS1 and/or EBS2. Nucleotide integrases in which the group II intron RNA has nucleotide base changes in the sequences of EBS1 or EBS2, as compared to the wild type, typically have altered specificity for the intended nucleic acid substrate.

Figure 2:
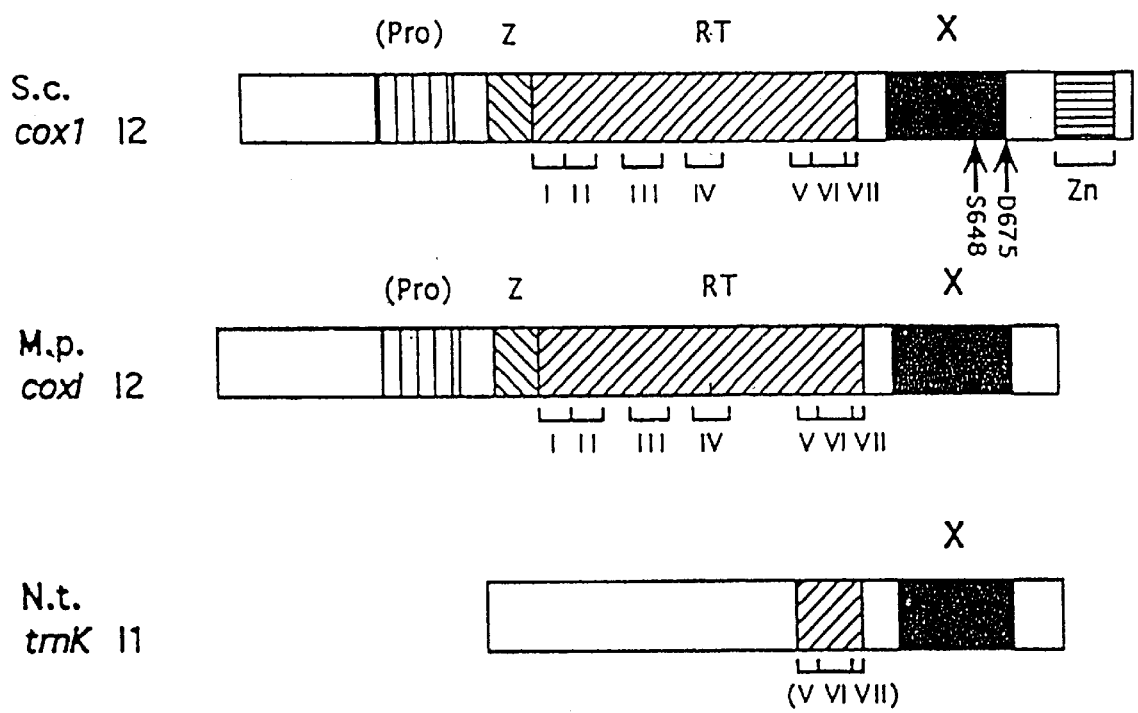
FIG. 2 is a schematic representation of the domains in three representative group II-intron encoded proteins, namely the protein which is encoded by the ORF sequence of the group II intron 2 of the *S. cerevisiae* mitochondrial COX1 gene, the group II intron 2 of the *M polymorpha* mitochondrial COX1 gene, and the group II intron 1 of the *N. tabacum* chloroplast trnK gene.

The group II intron-encoded protein. has an X domain, a reverse transcriptase domain, and, preferably, a Zn domain. The X domain of the protein has a maturase activity. The Zn domain of the protein has $Zn^{2+}$ finger-like motifs. As used herein, a group II intron-encoded protein includes modified group II intron-encoded proteins that have additional amino acids at the N terminus, or C terminus, or alterations in the internal regions of the protein as well as wild-type group II intron-encoded proteins. The domains of three representative group II intron-encoded proteins are depicted in FIG. 2.

The RNP particles having nucleotide integrase activity cleave single-stranded RNA molecules, single-stranded DNA molecules, and double-stranded DNA molecules. The RNP particles having nucleotide integrase activity also insert the group II intron RNA subunit of the RNP particle into the cleavage site. Thus, RNP particles having nucleotide integrase activity both cleave nucleic acid substrates and insert nucleic acid molecules into the cleavage site. With double-stranded DNA substrates, the nucleotide integrase inserts the group II intron RNA into the first strand, i.e., the strand that contains the IBS1 and IBS2 sequences, of the cleaved DNA substrate and, preferably, a cDNA molecule into the second strand of the cleaved DNA substrate.

The excised group II intron RNA subunit of the nucleotide integrase catalyzes cleavage of the single-stranded-substrates and the first strand of the double-stranded DNA substrate. The cleavage that is catalyzed by the excised group II intron RNA also results in the insertion, either partially or completely, of the excised group II intron RNA into the cleavage site, i.e. between nucleotide +1, which is immediately downstream of the cleavage site, and nucleotide −1, which is immediately upstream of the cleavage site. The group II intron-encoded protein subunit catalyzes cleavage of the second strand of the double-stranded DNA substrate. The second strand of the double stranded DNA substrate is cut at a position from about 9 to about 11 base pairs downstream of the cleavage site in the first strand, i.e. at a site between nucleotide positions +9, +10, and +11. It is believed that the group II intron-encoded protein also assists cleavage of the first strand of the double stranded DNA substrate by stabilizing the group II intron RNA. Thus, the RNP particle having nucleotide integrase activity is active under conditions that are similar to physiological conditions.

To cleave the substrates, it is preferred that the EBS1 and EBS2 sequences of the group II intron RNA of the nucleotide integrase have at least 90% complementarity, preferably full complementarity, with the IBS1 and IBS2 sequences, respectively, of the intended substrate. Thus, if there is not at least 90% complementarity between the EBS sequences of the excised group II intron RNA and IBS sequences of the intended substrate, it is preferred that nucleotide base changes be made in the non-complementary EBS sequences. To cleave single-stranded and double-stranded nucleic acid substrates efficiently, it is preferred that the nucleotide delta, which immediately precedes the first nucleotide of EBS1 be complementary to the nucleotide at +1 in the target site. Thus, if the delta nucleotide is not complementary to the nucleotide at +1 in the target site, the group II intron RNA is modified to contain a delta nucleotide which is complementary to the nucleotide at +1 on the sense strand of the substrate. To cleave double stranded DNA substrates efficiently, it is preferred that the target site has a sequence that is recognized by the group II intron-encoded protein of the nucleotide integrase. For example, cleavage of a double-stranded DNA substrate is achieved with a nucleotide integrase comprising a wild-type L1.ltrB RNA and LtrA protein if the first strand of the substrate contains the sequence, 5'-TCGATCGTGAACACATCCATAACC'3', SEQ.ID.NO. 13. which represents the sequence from −23 to +1 in the target site of the first strand.

A. Preparation of the Nucleotide Integrase by Isolation from a Genetically-Engineered Cell.

In one embodiment, RNP particles having nucleotide integrase activity are made by introducing an isolated DNA molecule which comprises a group II intron DNA sequence into a host cell. Preferably, the DNA molecule further comprises an IBS1 sequence and an IBS2 sequence just upstream of the 5' end of the group II intron DNA sequence to allow splicing of the group II intron RNA from a transcript of the group II intron DNA sequence. Suitable DNA molecules include, for example, viral vectors, plasmids, and linear DNA molecules. Following introduction of the DNA molecule into the host cell, the group II intron DNA sequence is expressed in the host cell such that excised RNA molecules encoded by the introduced group II intron DNA sequence and protein molecules encoded by introduced group II intron DNA sequence are formed in the cell. The excised group II intron RNA and group II intron-encoded protein are combined within the host cell to produce an RNP particle having nucleotide integrase activity.

Preferably, the introduced DNA molecule also comprises a promoter, more preferably an inducible promoter, operably linked to the group II intron DNA sequence. Preferably, the DNA molecule further comprises a sequence which encodes a tag to facilitate isolation of the RNP particles having nucleotide integrase activity, such as, for example, an affinity tag and/or an epitope tag. Preferably, the tag sequences are at the 5' or 3' end of the open reading frame sequence. Suitable tag sequences include, for example, sequences which encode a series of histidine residues, the Herpes simplex glycoprotein D, i.e., the HSV antigen, or glutathione S-transferase. An especially suitable tag is a sequence which encodes the intein from the *S. cerevisiae* VMA1 gene linked to the chitin binding domain from *Bacillus circulars*. Typically, the introduced DNA molecule also comprises nucleotide sequences that encode a replication origin and a selectable marker. Optionally, the introduced DNA molecule comprises sequences that encode molecules that modulate expression, such as for example T7 lysozyme.

The DNA molecule comprising the group II intron sequence is introduced into the host cell by conventional methods, such as, by cloning the DNA molecule into a vector and by introducing the vector into the host cell by conventional methods, such as electroporation or by $CaCl_2$-mediated transformation procedures. The method used to introduce the DNA molecule depends on the particular host cell used. Suitable host cells are those which are capable of expressing the group II intron DNA sequence. Suitable host cells include, for example, heterologous or homologous bacterial cells, yeast cells, mammalian cells, and plant cells. In those instances where the host cell genome and the group II intron DNA sequence use different genetic codes, it is preferred that the group II intron DNA sequence be modified to comprise codons that correspond to the genetic code of the host cell. The group II intron DNA sequence, typically, is modified by using a DNA synthesizer or by in vitro site directed mutagenesis, such as by PCR mutagenesis, to prepare a group II intron DNA sequence with different codons. Alternatively, to resolve the differences in the genetic code of the intron and the host cell, DNA sequences that encode the tRNA molecules which correspond to the genetic code of the group II intron are introduced into the host cell. Optionally, DNA molecules which comprise sequences that encode factors that assist in RNA or protein folding, or that inhibit RNA or protein degradation are also introduced into the cell.

The DNA sequences of the introduced DNA molecules are then expressed in the host cell to provide a transformed host cell. As used herein the term "transformed cell" means a host cell that has been genetically engineered to contain and express additional DNA, primarily heterologous DNA, and is not limited to cells which are cancerous. Then the RNP particles having nucleotide integrase activity are isolated from the transformed host cells.

The RNP particles having nucleotide integrase activity are isolated, preferably by lysing the transformed cells, such as by mechanically and/or enzymatically disrupting the cell membranes of the transformed cell. Then the cell lysate is fractionated into an insoluble fraction and soluble fraction. Preferably, an RNP particle preparation is isolated from the soluble fraction. The RNP particle preparations include the RNP particles having nucleotide integrase activity as well as ribosomes, mRNA and tRNA molecules. Suitable methods for isolating RNP particle preparations include, for example, centrifugation of the soluble fraction through a sucrose cushion. The RNP particles, preferably, are further purified from the RNP particle preparation or from the soluble fraction by, for example, separation on a sucrose gradient, or a gel filtration column, or by other types of chromatography. For example, in those instances where the group II-intron encoded protein subunit of the desired RNP particle has been engineered to include a tag, the RNP particles having nucleotide integrase activity are purified from the particle preparation by affinity chromatography on a matrix which recognizes and binds to the tag. For example, NiNTA SuperflowTH from Qiagen, Chatsworth Calif., is suitable for isolating RNP particles having nucleotide integrase activity when the group II intron-encoded protein has a histidine tag. It has been found that the a system which employs a chitin column and an intein and chitin binding domain tag on the group II intron-encoded protein results in the production of RNP particles that are substantially pure, i.e., the intron encoded protein represents at least 95% of the protein in the RNP particles eluted from the column. Thus, the latter system is particularly suitable for isolating RNP particles having nucleotide integrase activity.

B. Preparation of the Nucleotide Integrase by Combining Exogenous RNA with a Group II Intron-Encoded Protein to Form a Reconstituted RNP Particle In another embodiment, the nucleotide integrase is formed by combining an isolated exogenous RNA with an isolated group II intron-encoded protein in vitro to provide a reconstituted RNP particle having nucleotide integrase activity. The exogenous RNA is made by in vitro transcription of the group II intron DNA. The exogenous RNA may be made by in vitro transcription of the group II intron DNA only, i.e. the transcript lacks flanking exon sequences. Alternatively, the exogenous RNA is made by in vitro transcription of the group II intron DNA and the DNA of all, or portions, of the flanking exons to produce an unprocessed transcript which contains the group II intron RNA and the RNA encoded by the flanking exons or portions thereof. Then the exogenous RNA is spliced from the unprocessed transcript.

The purified group II intron-encoded protein is prepared by introducing into a host cell an isolated DNA molecule that comprises at least the open reading frame sequence of a group II intron. The DNA molecule may comprise a group II intron ORF sequence operably linked to an inducible promoter. Alternatively, the DNA molecule may comprise a group II intron DNA sequence. Preferably, the introduced DNA molecule also comprises a sequence at the 5' or 3' end of the group II intron ORF sequence which, when expressed in the host cell, provides an affinity tag or epitope on the N-terminus or C-terminus of the group II intron-encoded protein. Thus, the DNA molecule may comprise at the 5' or 3' end of the ORF, for example, a sequence which encodes a series of histidine residues, or the HSV antigen, glutathione-S-transferase, or an intein linked to a chitin binding domain. Typically, the DNA molecule also comprises nucleotide sequences that encode a replication origin and a selectable marker.

When the introduced DNA molecules comprise a group II intron ORF sequence operably linked to an inducible promoter, the ORF sequence is then expressed in the host cell, preferably by adding a molecule which induces expression, to provide a host cell that contains RNP particles comprising the group II intron-encoded protein associated with endogenous nucleic acids, particularly endogenous RNA molecules. Then the transformed cell is lysed, and preferably fractionated into a soluble fraction and an insoluble fraction. The RNP particles comprising the protein and the endogenous RNA are then isolated, preferably from the soluble fraction, preferably by using methods such as affinity chromatography. The RNP particles are then incubated with the exogenous RNA, preferably in a buffer, to allow the exogenous RNA to displace the associated RNA molecules and to form RNP particles having nucleotide integrase activity. Optionally, the RNP particles, are treated with a nuclease to remove the RNA that is associated with the group II intron encoded protein prior to incubation of the protein preparation with the exogenous RNA. The RNP particles may be treated with the nuclease by adding the nuclease to the soluble fraction. Alternatively, the RNP particles may be treated with the nuclease after isolation of the RNP particles from the soluble fraction.

When DNA molecules comprise a splicing-competent group II intron sequence, are introduced and expressed in the host cells, RNP particles comprising a group II intron-encoded protein associated with an excised group II intron RNA that encodes the protein are produced. When DNA molecules comprise a splicing-defective group II intron sequence, are introduced and expressed in the host cells, the group II intron-encoded protein is not associated with an excised, group II intron RNA that encodes the protein The RNP particles that are produced when a splicing-defective group II intron DNA sequence is introduced and expressed in a host cell comprise other types of RNA molecules, such as for example, unspliced group II intron RNA molecules that encode the protein, ribosomal RNA molecules, mRNA molecules, tRNA molecules or other nucleic acids. Following formation of the RNP particles in the host cell, the transformed cell is lysed, and preferably fractionated into a soluble fraction and an insoluble fraction. The RNP particles comprising the protein are then isolated, preferably from the soluble fraction, preferably by using methods such as affinity chromatography. The isolated RNP particles are then treated with a nuclease that degrades all of the endogenous RNA molecules. Preferably the RNP particles are treated with a nuclease which can be chemically inactivated, such as for example, micrococcal nuclease. The group II intron-encoded protein preparation is then combined with the exogenous RNA, preferably in a buffer, to allow formation of RNP particles having nucleotide integrase activity These methods enable production of increased quantities of nucleotide integrases. Conventional methods produce approximately 0.1 to 1 µg of an RNP particles having nucleotide integrase per liter of cultured cells. However, these RNP particles are highly contaminated with other proteins. The methods of the present invention enable the production of at least 0.5 mg of RNP particles having nucleotide integrase activity per liter of cultured cells. Moreover, the RNP particles having nucleotide integrase activity produced in accordance with the present methods are substantially pure, i.e., at least 95% of the protein in the final RNP particle preparation is the group II intron-encoded protein. The present methods also offer the further advantage of permitting the sequences of the RNA component and the protein component of the nucleotide integrase to be readily modified. Typically, the nucleotide integrases are modified by introducing nucleotide base changes, deletions, or additions into the group II intron RNA by PCR mutagenesis of the group II intron.

The following examples of methods for preparing a group II intron-encoded protein and for preparing nucleotide integrases are included for purposes of illustration and are not intended to limit the scope of the invention.

Preparing Nucleotide Integrases By Coexpression of a Group II Intron RNA and a Group II Intron Encoded Protein

EXAMPLE 1

Figure 3:
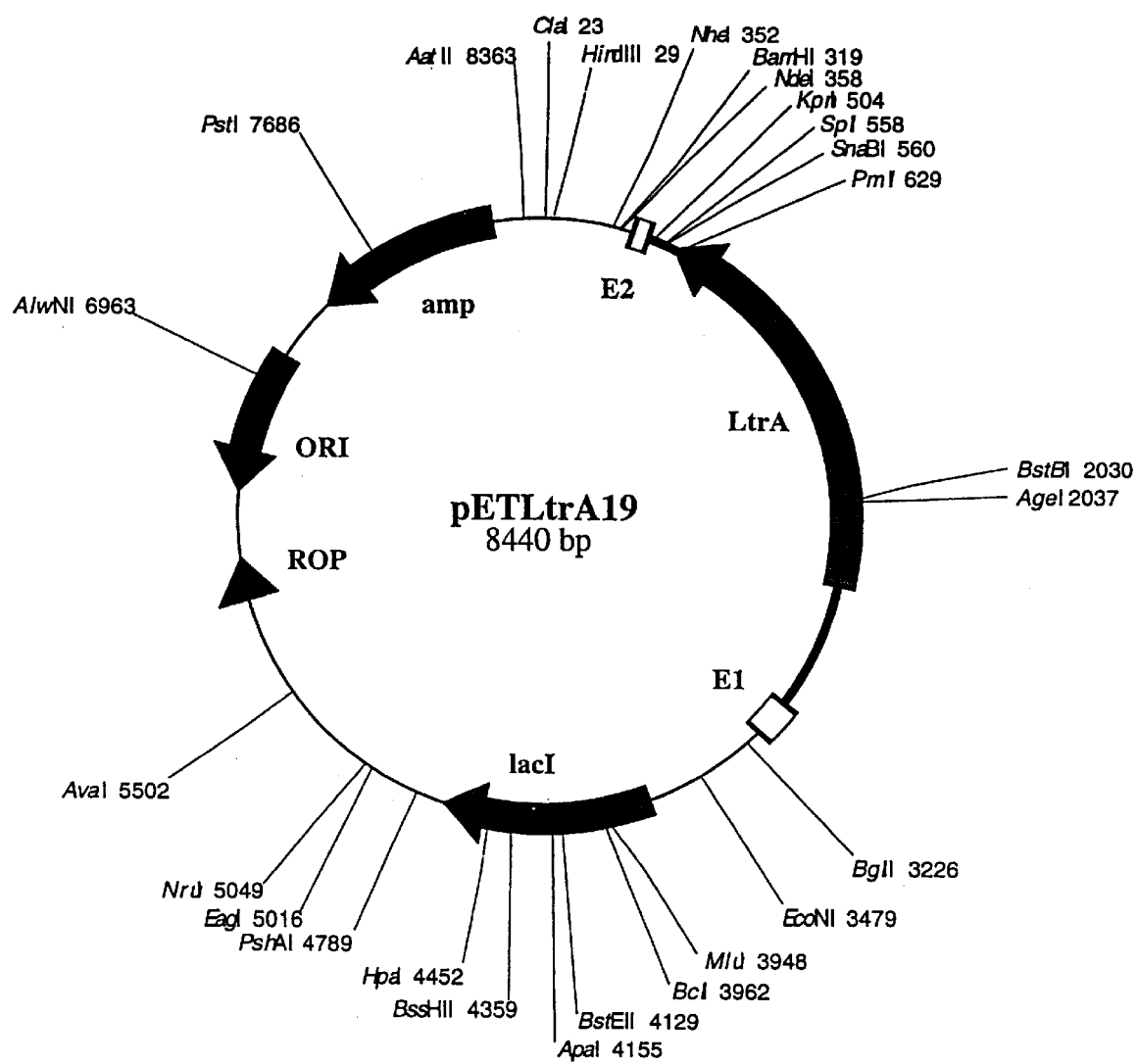
FIG. 3 is the plasmid map of pETLtrAl9.

RNP particles having nucleotide integrase activity and comprising an excised RNA that is encoded by the L1.ltrB intron of a lactococcal cojugative element pRSO1 of *Lactococcus lactis* and the protein encoded by the ORF of the L1.ltrB intron were prepared by transforming cells of the BLR(DE3) strain of the bacterium *Escherichia coli*, which has the recA genotype, with the plasmid pETLtrAl9. Plasmid pETLtrAl9, which is schematically depicted in FIG. 3, comprises the DNA sequence for the group II intron L1.ltrB from *Lactococcus lactis*, shown as a thick line, positioned between portions of the flanking exons ltrBE1 and ltrBE2, shown as open boxes. pETLtrAl9 also comprises the DNA sequence for the T7 RNA polymerase promoter and the T7 transcription terminator. The sequences are oriented in the plasmid in such a manner that the ORF sequence, SEQ. ID. NO. 2, within the L1.ltrB intron is under the control of the T7 RNA polymerase promoter. The ORF of the L1.ltrB intron, shown as an arrow box, encodes the protein LtrA. The sequence of the L1.ltrB intron and the flanking exon sequences present in pETLtrAl9 are shown in FIG. 4 and SEQ. ID. NO. 1. Vertical lines in FIG. 4 denote the junctions between the intron and the flanking sequences. The amino acid sequence of the LtrA protein, SEQ. ID. NO. 3 is shown under the ORF sequence, SEQ. ID. NO. 2, in FIG. 4. The sequences of EBS1 and EBS2 include nucleotides 457 through 463 (EBS1), nucleotides 401 through 406 (EBS2a), and nucleotides 367 through 372 (EBS2b). Domain IV is encoded by nucleotide 705 to 2572.

pETLtrAl9 was prepared first by digesting pLE12, which was obtained from Dr. Gary Dunny from the University of Minnesota, with HindIII and isolating the restriction fragments on a 1% agarose gel. A 2.8 kb HindIII fragment which contains the L1.ltrB intron together with portions of the flanking exons ltrBE1 and ltrBE2 was recovered from the agarose gel and the single-stranded overhangs were filled in with the Klenow fragment of DNA polymerase I obtained from Gibco BRL, Gaithersburg, Md. The resulting fragment was ligated into plasmid pET-11a that had been digested with XbaI and treated with Klenow fragment. pET-11a was obtained from Novagen, Madison, Wis.

pETLtrAl9 was introduced into the *E. coli* cells using the conventional $CaCl_2$-mediated transformation procedure of Sambrook et al. as described in "Molecular Coning A Laboratory Manual", pages 1–82, 1989 . Single transformed colonies were selected on plates containing Luria-Bertani (LB) medium supplemented with ampicillin to select the plasmid and with tetracycline to select the BLR strain. One colony was inoculated into 2 ml of LB medium supplemented with ampicillin and grown overnight at 37° C. with shaking. 1 ml of this culture was inoculated into 100 ml LB medium supplemented with ampicillin and grown at 37° C. with shaking at 200 rpm until $OD_{595}$ of the culture reached 0.4. Then isopropyl-beta-D-thiogalactoside was added to the culture to a final concentration of 1 mM and incubation was continued for 3 hours. Then the entire culture was harvested by centrifugation at 2,200×g, 4° C., for 5 minutes. The bacterial pellet was washed with 150 mM NaCl and finally resuspended in 1/20 volume of the original culture in 50 mM Tris, pH 7. 5, 1 mM EDTA, 1 mM DTT, and 10% (v/v) glycerol (Buffer A)and 2 mg/ml lysozyme. Bacteria were frozen at −70° C.

To produce a lysate the bacteria were thawed and frozen at −70° C. three times. Then 4 volumes of 500 mM KCl, 50 mM $CaCl_2$, 25 mM Tris, pH 7.5, and 5 mM DTT (HKCTD) were added to the lysate and the mixture was sonicated until no longer viscous, i.e. for about 5 seconds or longer. The lysate was fractionated into a soluble fraction and insoluble fraction by centrifugation at 14,000×g, 4° C., for 15 minutes. Then 5 ml of the resulting supernatant, i.e., the soluble fraction, were loaded onto a sucrose cushion of 1.85 M sucrose in HKCTD and centrifuged for 17 hours at 4° C., 50,0000 rpm in a Ti 50 rotor from Beckman. The pellet which contains the RNP particles was washed with 1 ml water and then dissolved in 25 µl 10 mM Tris, pH 8. 0, 1 mM DTT on ice. Insoluble material was removed by centrifugation at 15, 000×g, 4° C., for 5 minutes. The result is a preparation of partially-purified RNP particles that comprise the excised L1.ltrB intron RNA and the LtrA protein The yield of RNP particles was 25 to 50 $O.D._{260}$ units (~16 µg protein) per 100 ml culture, with 1 $O.D._{260}$ units of RNPs containing 0.3 to 3 µg LtrA protein. To minimize nuclease activity, the partially-purified RNPs were further purified by an additional centrifugation through a 1.85 M sucrose cushion, as described above.

EXAMPLE 2

RNP particles having nucleotide integrase activity and comprising the LtrA protein and the excised L1.ltrB intron RNA were prepared as described in example 1 except the plasmid pETLtrAl9 was used to transform cells of the BL21(DE3) strain of *E. coli*. The transformed cells were fractionated into a soluble fraction and an insoluble fraction as described in Example 1 to provide a preparation of RNP particles having nucleotide integrase activity

EXAMPLE 3

RNP particles having nucleotide integrase activity and comprising the LtrA protein and the excised L1.ltrB intron RNA were prepared by transforming cells of the *E. coli* strains BLR(DE3) with pETLtrAl9 as described in Example 1 except that the transformed *E. coli* were grown in SOB medium and shaken at 300 rpm during the 3 hour incubation. The transformed cells were fractionated into a soluble fraction and an insoluble fraction as described in Example 1 to provide a preparation of RNP particles having nucleotide integrase activity

EXAMPLE 4

RNP particles having nucleotide integrase and comprising the LtrA protein and the excised L1.ltrB intron RNA were prepared as described above in sample 1 except that the plasmid pETLtrAl9 was used to transform cells of the *E. coli* strain BL21(DE3). The cells were also transformed with plasmid pOM62 which is based on the plasmid pACYC184 and has an approximately 150 bp insert of the argU(dnaY) gene at the EcoRI site. The argU gene encodes the tRNA for the rare arginine codons AGA and AGG. The LtrA gene contains 17 of the rare arginine codons. The transformed cells were grown in SOB medium and fractionated into a soluble fraction and an insoluble fraction as described in Example 1 to provide a preparation of RNP particles having nucleotide integrase activity.

EXAMPLE 5

RNP particles having nucleotide integrase and comprising the excised L1.ltrB intron RNA and the LtrA protein were prepared by transforming host cells as described above in Example 1 except that the LtrA ORF was tagged at the C-terminus with a $His_6$ affinity tag and an epitope derived from the Herpes simplex virus glycoprotein D. The tag is used to facilitate isolation of the RNP particles. The plasmid adding the tags was made in two steps by using PCR. In the first step, a fragment containing exon 1 and the LtrA ORF was amplified using primers LtrAex1.Xba having the sequence 5'TCACCTCATCTAGACATTTTCTCC 3', SEQ. ID. NO. 5 which introduces an Xba I site in exon 1 of LtrB, and LtrAexpr3 5'CGTTCGTAAAGCTAGCCTTGTGTT-TATG 3', SEQ. ID. NO. 6, which substitutes a CGA (arginine) codon for the stop codon and introduces an Nhe I site at the 3' end of the LtrA ORF. The PCR product was cut with XbaI and Nhe I, and the restriction fragments gel purified and cloned into pET-27b(+), cut with Xba I and Nhe I obtained from Novagen, Madison, Wis. The resulting plasmid pIntermediate-C fuses the 3' end of the LtrA ORF to an HSV tag and $His_6$ purification tag, both of which are present on the vector pET-27b(+). In a second step, intron sequences 3' to the ORF and exon 2 are amplified using pLE12 as a template and the 5' primer LtrAConZnl, having the sequence 5'CACAAGTGATCATTTACGAACG 3', SEQ. ID. No. 7 and the 3' primer LtrAex2, which has the sequence 5'TTGGGATCCTCATAAGCTTT GCCGC 3', SEQ. ID. NO. 8. The PCR product is cut with BclI and BamHI, the resulting fragment filled in, gel purified and cloned into pIntermediate-C, which has been cleaved with Bpul 102I and filled in. The resulting plasmid is designated pC-hisLtrAl9.

Cells of the BLR(DE3) strain of E. coli were transformed as described in example 1 with pIntermediate-C and cultured at 37° C. for 3 hours in SOB medium as described in example 3. The cells were also fractionated into a soluble fraction, which contains RNP particles having nucleotide integrase activity, and an insoluble fraction as described in example 1. The RNP particles were further purified as described in example 1.

EXAMPLE 6

RNP particles having nucleotide integrase activity and comprising an excised L1.ltrB intron RNA and the LtrA protein were prepared by transforming host cells as described above in example 1 except that the LtrA ORF was tagged at the N-terminus with a $His_6$ affinity tag and the epitope tag XPRESS™ which was obtained from Invitrogen, San Diego, Calif. The tag is used to facilitate isolation of the RNP particles. The plasmid adding the tags was made in two steps by using PCR. In the first step, a fragment was made in two steps by using PCR mutagenesis. In the first step, the LtrA ORF and 3' exon were amplified and BamHI sites were appended to both the 5' an 3' end of the LtrA ORF using pLE12 as a substrate and the following pair: 5' primer N-LtrA 5', having the sequence 5° C.AAAG-GATCCGATGAAACCA ACAATGGCAA 3', SEQ. ID. NO. 9; and the 3' primer LtrAex2, SEQ. ID. NO. 8. The PCR product was cut with BamHI and the resulting restriction fragment was gel purified and cloned into the BamHI site of plasmid pRSETB obtained from Invitrogen, San Diego, Calif. The resulting plasmid pIntermediate-N fuses the N terminus of the LtrA ORF to a $His_6$ purification tag, and adds an XPRESS™ epitope tag from the vector. In a second step, the 5' exon and L1.ltrB intron sequences 5' to the ORF were amplified using pLE12 as a substrate and the 5' primer NdeLTR5, having the sequence 5'AGTGGCTTCCATAT-GCTTGGTCATCACCTCATC 3', SEQ. ID. No. 10 and 3' primer NdeLTR3', which has the sequence 5' GGTAGAAC-CATATGAAATTCCTCCTCCCTAATCAATTTT 3', SEQ. ID. NO. 11. The PCR product was cut with Nde I, the fragment gel purified and cloned into pIntermediate-N, which had also been cut with Nde I. Plasmids were screened for the orientation of the insert, and those oriented such that the 5' exon was proximal to the T7 promoter were used to transform the host cells. The resulting plasmid pFinal-N expresses a message under the control of the T7 polymerase promoter which comprises the E1 and E2 portions of the exons 1 LtrBE1 and LtrBE2, and the LtrA ORF fused at the 5'end with an $His_6$ purification tag and the XPRESS™ epitope tag.

Cells of the BLR(DE3) strain of E. coli were transformed as described in example 1 with pIntermediate-N and cultured at 37° C. f or 3 hours in SOB medium as described in example 3. The cells were also fractionated into a soluble fraction, which contains RNP particles having nucleotide integrase activity, and an insoluble fraction as described in example 1. The RNP particles were further purified as described in example 1.

EXAMPLE 7

RNP particles having nucleotide integrase activity and comprising an excised L1.ltrB intron RNA and the LtrA protein were prepared as described by transforming host cells as described above in example 1 except that the LtrA ORF was tagged at the C-terminus with an intein from Saccharomyces cerevisiae VMA1 gene and the chitin binding domain (CBD) from Bacillus circulans. The tag was used to facilitate purification of the RNP particles and was added using components of the Impact™ purification system obtained from New England Biolabs, Beverly, Mass. A plasmid adding the tags was made in two steps by using PCR. In the first step, the LtrA ORF was amplified by PCR using pETLtrAl9 as template and using 5' primer LtrAexpr, 5'-AAACCTCCATATGAAACCAACAATG-3', SEQ. ID. NO. 12 and 3' primer ltrimpact: 5'TAACTTCCCGGGCTTGTGTTTATGAATCAC-3', SEQ. ID. NO. 14 which deletes the termination codon and introduces a SmaI site. The PCR product was cut with NdeI and SmaI and cloned into pCYB2, obtained from New England Biolabs, Beverly, Mass, and cleaved with the same enzymes. Colonies were screened for inserts and two independent colonies with the desired insert were retained to yield pLI1PInt21 and pLI1PInt22. In a second step, pLI1PInt21 was cleaved with PstI, the overhangs repaired with T4 DNA polymerase in the presence of 0.2 mM dNTPs. The DNA was then phenol extracted, ethanol precipitated and then partially digested with Pml I. The approximately 1580 bp PmlI- Pst I fragment was cloned into pETLtrAl9 digested with Pml I. The clones with correct insert were screened and one oriented such that the intein is fused to the C terminus of the LtrA ORF was called pLI1Int. The resulting construct expresses the L1.ltrB intron and fuses the LtrA ORF with the sequences that encode VMAI intein and CBD.

Cells of the BLR(DE3) strain of E. coli were transformed as described in example 1 with pL1Int. The transformants were restreaked on ampicillin selective plates and single colonies were inoculated into 50 mL of LB medium and grown overnight at 37° C. This culture was used to inoculate 0.5 liters of SOB in 4 liter flasks at a 1:100 dilution. The cultures were grown to an $OD_{595}$ 0.7–1.0 and induced with 1 mM IPTG at room temperature for 4 hours. The cultures were harvested, washed with 150 mM NaCl 10 mM Tris-HCl (pH 7.5), and repelleted and stored in 50 ml of Buffer I (20 mM Tris-HCl (pH8.0), 0.5 M NaCl, 0.1 mM EDTA, 0.1% NP-40). The cells were broken by sonicating for 1 minute 3 times in a Bronson sonicator at setting 7. The lysate was cleared by centrifugation at 12,000×g for 30 minutes. The cleared lysate was loaded on a chitin affinity column equilibrated with Buffer I. The RNP particles comprising a tagged protein are retained on the column. Then 15 ml of elution buffer (Buffer I+30 mM DTT) was passed through the column, the column flow was stopped, and the column incubated overnight at 4° C. to allow self-cleavage of the intein tag and release of the purified RNP particles from the chitin. Flow was restarted and the RNP particles comprising an excised L1.ltrB intron RNA and the LtrA protein were collected.

EXAMPLE 8

RNP particles having nucleotide integrase activity and comprising the LtrA protein and an excised L1.ltrB intron RNA having an altered EBS1 sequence were prepared as described above in example 1 except that the cells were transformed and the RNP particles were made using pLI1-EBS1/-6C. The pLI1-EBS1/-6C construct which has a single nucleotide change G to C at position 6 in the EBS1 (G3137C as based on Mills et al, 1996) sequence of the wild-type intron and a complementary change in the 5' exon at position –6 relative to the 5' splice site to permit splicing was constructed via two PCR steps. In the first step pETLtrAl9 was subjected to PCR with primers OP2, 5'-GGATCGAGATCTCGATCCCG, SEQ. ID. NO. 15 and IP11: 5'CGCACGT TATCGATGTGTTCAC, SEQ. ID. NO. 16 to introduce the single nucleotide change in the exon, and with primers IP4, 5'-TTATGGTTGTCGACTTATCTGTTATC, SEQ.ID.NO. 17. and OP1, OP1: 5'-CTTCGAATACCGGTTCATAG, SEQ. ID. NO. 18 to introduce the single nucleotide change in EBS1. The single nucleotide change in the IP4 primer introduces a SalI site in the EBS1 sequence, which was subsequently used to identify the desired clones. The second PCR step was performed using the above two PCR products as Primers and pETLtrAl9 DNA linearized with BglII and BamHI as the template. The second PCR product was reamplified with flanking primers OP2 and OP1 using Pfu polymerase from Stratagene and digested with BglII and BsrGI to yield a 554-bp fragment that was cloned between the BsrGI and BglII sites of pETLtrAl9. The desired clones were identified by digestion with HindIII and SalI, and the region that had been generated by PCR was sequenced completely to insure that no adventitious mutations had been introduced.

EXAMPLE 9

Figure 5:
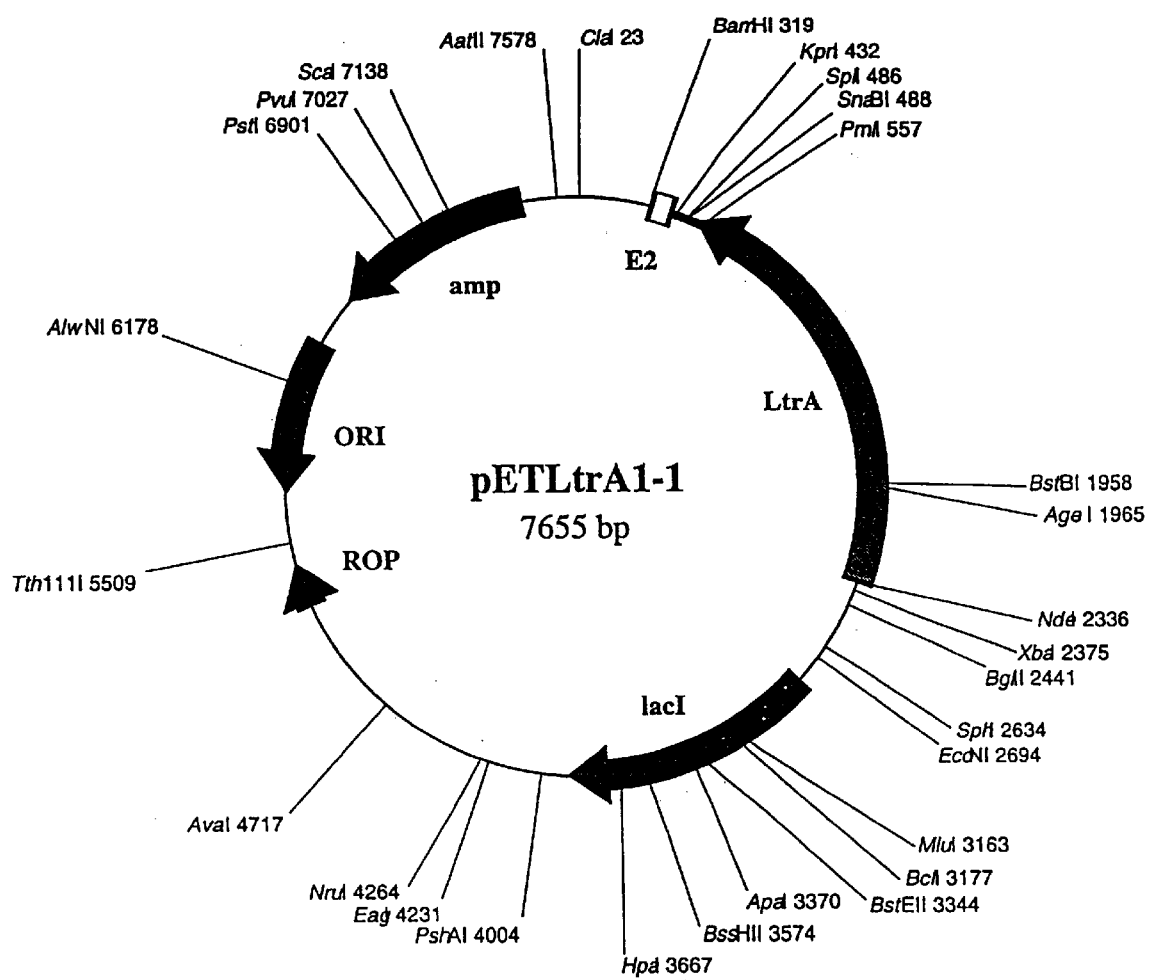
FIG. 5 is the plasmid map of plasmid pETLtrAl-1.
Figure 6:
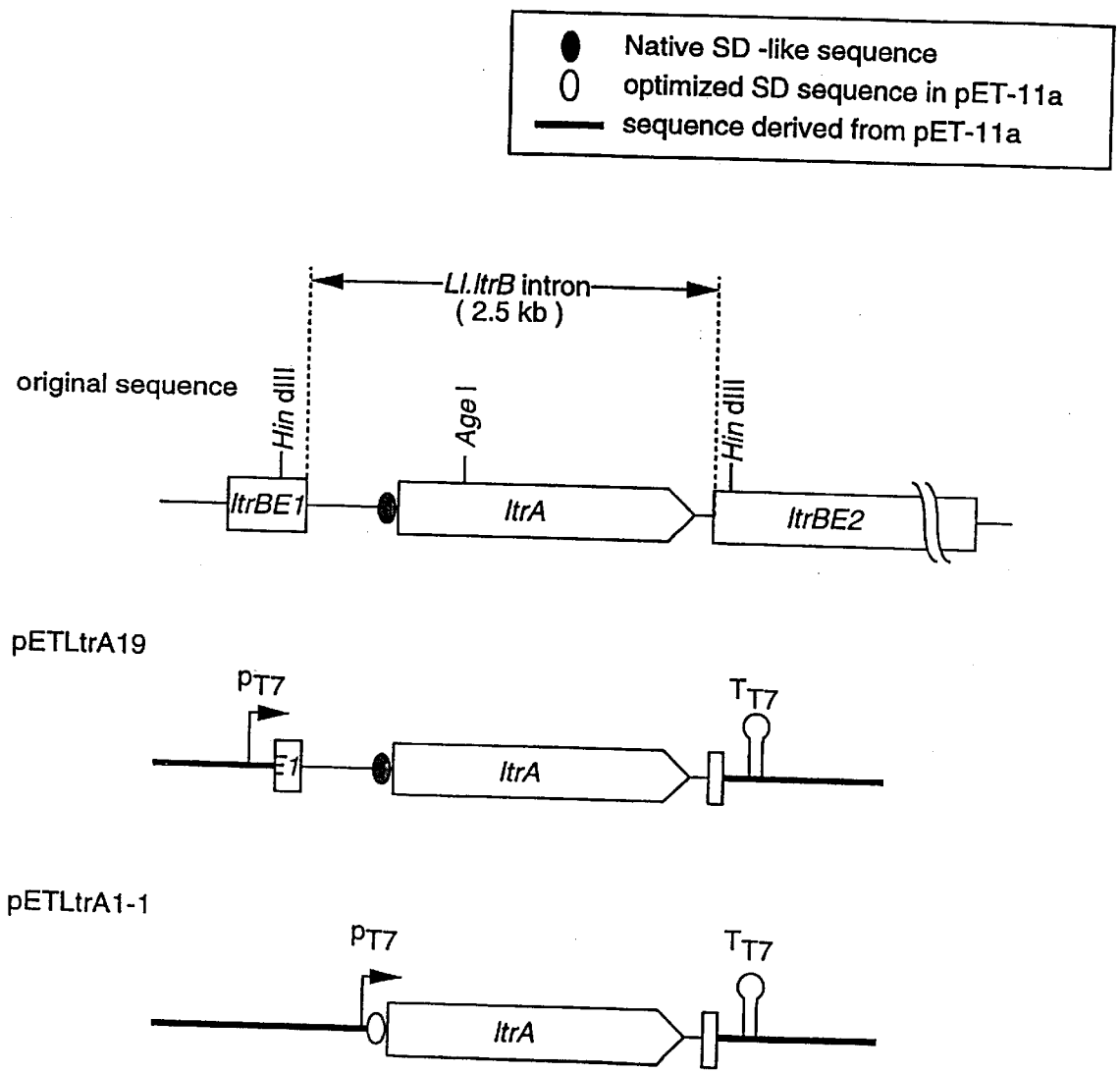
FIG. 6 is a schematic representation of the inserts in pLE12, pETLtrAl9 and pETLtrAl-1.

A partially-purified preparation of the LtrA protein, which is encoded by the ORF of the L1.ltrB intron, using plasmid pETLtrAl1 was prepared. Plasmid pETLtrAl-1 is a derivative of pETLtrAl9 and lacks exon 1 and the intron sequences upstream of the LtrA ORF. Accordingly, the LtrA ORF is directly downstream of the phage T7 promoter following the Shine-Dalgarno sequence in the plasmid. The plasmid map of pETLtrAl-1 is shown in FIG. 5.

pETLtrAl-1 was made by using the polymerase chain reaction to amplify the LtrA ORF using the 5' primer LtrAexpr. SEQ.ID. 12, which introduces an NdeI site and 3' primer LtrAex2, SEQ. ID. NO. 8. The PCR product was cut with NdeI and BamHI, gel purified on a 1%. agarose gel, and cloned into pET-11a. The inserts of pLE12, pETLtrAl9 and pETLtrAl-1, each of which contain the LtrA ORF are depicted in FIG. 6.

pETLtrAl-1 was introduced into cells of the *E. coli* strain BLR(DE3) as described in Example 1 and the transformed cells grown for 3 hours in SOB medium at 37° C. as described in Example 3. Thereafter, the cells were lysed and the resulting lysate fractionated into a soluble fraction and insoluble fraction by low speed centrifugation as described in Example 1 to provide fractions containing a partially-purified preparation of LtrA protein.

Preparing Nucleotide Integrases using in vitro-synthesized intron RNA

EXAMPLE 10

RNP particles having nucleotide integrase activity and comprising an excised, L1.ltrB intron RNA which lacks the ORF and an LtrA protein was prepared by mixing an in vitro-synthesized intron RNA with an LtrA protein preparation that was made by digesting the RNP particles prepared as described above in example 1 with micrococcal nuclease (MN). Specifically, 1.0 O.D.$_{260}$ of the RNP particle preparation were resuspended in 40 μl of 10 mM Tris, HCl, pH 7.5, 10 mM MgCl$_2$, 2.5 mM CaCl$_2$, 5 mM DTT and incubated with 12 or 36 units of MN from Pharmacia for 10 minutes at 22° C., after which the MN was inactivated by addition of EGTA to 7.5 mM.

The group II intron RNA was generated by in vitro transcription of pLI2-ΔORF. pLI2-ΔORF, which has a large deletion in the intron ORF, was derived from pLI2 by inverse PCR with primers ΔORFa: 5'-GGGGGGGCTAGCACGCGTCGCCACGTAATAAA TATCTG GACG, SEQ. ID. NO. 19 and ΔORFb: 5'-GGGGGGGCTAGCACGCGTTGGGAAATG GCAATG ATAGC, SEQ.ID.NO. 20, each containing an MluI site. The PCR product was digested with MluI and self-ligated to generate pLI2-ΔORF, thereby replacing amino acids 40 to 572 of the LtrA ORF with threonine and arginine. The plasmid was linearized with BamHI and transcribed with phage T3 RNA polymerase, and the in vitro-synthesized RNA (30 to 50 μg) was spliced for 60 min at 42° C. in 100 l of 1 M NH$_4$Cl, 100 mM MgCl$_2$, and 50 mM Tris-HCl (pH 7.5). Prior to reconstitution, the RNA was heated to 85 to 90° C. for 2 minutes, then stored on ice.

0.05 O.D.$_{260}$ units of the MN-treated RNP particles was added to 20 μl of reaction medium containing 50 mM Tris-HCl (pH7.5), 10 mM MgCl$_2$, 10 mM KCl, 5 mM DTT, and 1 μg of the spliced RNA to provide RNP particles having nucleotide integrase activity and comprising a modified, excised, L1.ltrB intron RNA and an LtrA protein.

EXAMPLE 11

RNP particles having nucleotide integrase and comprising the LtrA protein and an excised L1.ltrB intron RNA having a kanamycin resistance gene inserted in domain IV in place of the LtrA ORF were prepared as described above in example 10 except that the RNA component was made using pLI2-ΔORFkan$^R$. pLI2-ΔORFkan$^R$, which replaces amino acids 39–573 of the LtrA ORF with a kan$^R$ gene, was constructed by cloning the 1,252-bp SalI fragment containing the kan$^R$ gene from pUK4K (Pharmacia, Piscataway, N.J.) into the MluI site of pL12-ORF by blunt-end ligation after filling in both the SalI and MluI sites with Klenow polymerase (Life Technologies, Gaithersburg, Md.)

Comparative Example A

RNP particles lacking nucleotide integrase activity were prepared as described in Example 1 from cells of the BLR(DE3) strain of *E. coli* that had been transformed with plasmid pET11a, which lacks a group II intron. Accordingly, is these RNP particles do not comprise excised, group II RNA or group II intron-encoded proteins and therefore, do not have nucleotide integrase activity.

Comparative Example B

RNP particles lacking nucleotide integrase activity were prepared as described in Example 1 from cells of the BLR(DE3) strain of *E. coli* that had been transformed with plasmid pETLtrAl9FS, which comprises the sequence of an LtrA ORF having a frame shift 372 base pairs downstream from the initiation codon of the LtrA ORF. frame. Accordingly, the RNP particles contain a truncated LtrA protein, i.e. an LtrA protein lacking the Zn domain and, therefore, do not have nucleotide integrase activity.

Characterization of the RNP particles of Examples 1 and 2

A portion of the RNP particle preparation of examples 1 and 2 and comparative examples A and B were subjected to SDS polyacrylamide gel electrophoresis. Staining of the resulting gel with Coomassie Blue permitted visualization of the proteins in each of the fractions. A band of approximately 70 kDa, which corresponds to the predicted molecular weight of the LtrA protein was seen in the lanes containing aliquots of the RNP particles of Examples 1 and 2. This band was absent from the lanes containing the RNP particles prepared from comparative examples A and B. On the basis of the staining intensity of the 70 kDa band, the quantity of LtrA protein in 10 $OD_{260}$ units of RNP particles was estimated to be approximately 3 μg. Thus, RNP particles containing the group II intron-encoded protein LtrA can be prepared by expression of the group II intron L1.ltrB in a heterologous host cell.

The reverse transcriptase activities of the RNP particles of examples 1 and 2 and the RNP particles of comparative examples A and B were assayed by incubating each of the RNP particle preparations with a poly(rA) template and oligo $(dT_{18})$ as a primer. The RNP particles of examples 1 and 2 exhibited reverse transcriptase activity, while the RNP particles of comparative examples A and B exhibited no reverse transcriptase activity. Thus, the methods described in examples 1 and 2 are useful for preparing RNP particles that have reverse transcriptase activity. The reverse transcriptase activity that is present in nucleotide integrases allows incorporation of a cDNA molecule into the cleavage site of the double stranded DNA which is cut by the nucleotide integrase.

Characterizing the Distribution and Yield of the LtrA Protein

A portion of the insoluble fraction and soluble fraction of the lysates from the cells transformed and cultured according to the methods described in examples 1, 2, 3, 4 and 9 were subjected to SDS polyacrylamide gel electrophoresis. Following electrophoresis, the SDS gels were stained with Coomassie blue to compare the yield of the LtrA protein and the distribution of the 70 kDa LtrA protein prepared by the methods of examples 1, 2, 3, 4 and 9. As shown on the gel, more of the LtrA protein was found in the soluble fraction when the transformed BLR (DE3) cells were grown in SOB medium and shaken at 300 rpm than when the transformed BLR cells were grown in LB medium and shaken at 200 rpm. In addition, the total amount of LtrA protein produced by the transformed BLR cells, that is the amount of LtrA in both the soluble and insoluble fractions, increased when, as described in example 4, a plasmid comprising the L1.ltrB intron and a plasmid comprising argu(dnaY) gene were both introduced into the host cells, the LtrA protein which was expressed in cells transformed with a plasmid which lacks the 5' segment of the L1.ltrB.intron, as described in example 9, was significantly more insoluble than the LtrA protein which was expressed in cells transformed with a plasmid that contained the 5'segment of the intron as well as the LtrAORF.

Characterization of the Group II Intron-Encoded Protein Prepared According to the Methods of Examples 5-and 6

A portion of the insoluble fraction and soluble fractions of the lysates from the cells transformed and cultured according to the methods described in examples 5 and 6 and in comparative examples A and B were subjected to electrophoresis on duplicate SDS-polyacrylamide gels. One of the gels was stained with Coomassie blue and the proteins on the duplicate were transferred to nitrocellulose paper by Western blotting. A primary antibody to the HSV antigen and an alkaline phosphatase-labeled anti-mouse IgG secondary antibody were used in an enzyme-linked immunoassay to identify proteins carrying the HSV epitope or the Xpress™ tag. The anti-HSV antibody and the anti-Xpress™ tag antibody bound to a protein having a molecular weight of approximately 70 kDa, which is close to the calculated molecular weight of the LtrA protein. The HSV tagged LtrA protein and the Xpress™ tagged LtrA protein were found in the soluble and insoluble fractions from cells transformed with pIntermediateC and pIntermediateN but not in the soluble fractions and insoluble fractions of cells transformed with pET27b(+) and pRSETB. Thus, the methods of examples 5 and 6 are useful for preparing an RNP particle comprising a tagged group II intron encoded protein. These assays also demonstrated that the amount of the tagged group II intron-encoded protein present in the soluble fraction, from which the RNP particles are derived, increases when the transformed and induced cells are incubated at 22° C. as compared to 37° C. In cells grown at 22° C., the yield of the tagged protein was 0.4 to 2 mg per 1 culture, which is 2 to 5% of the total protein, with about 30% being soluble and 40 to 90% of the soluble protein being recovered in RNP particles (0.3 to 3 μg LtrA protein/$O.D._{.260}$). In cells grown at 37° C., a high proportion of the protein was insoluble. However, a significant amount of the tagged LtrA protein that was found in the soluble fraction was present in RNP particles.

Characterization of the Purity and Yield of the Protein in the RNP Particles Prepared According to the Method of Example 7

A portion of the RNP particle preparation of example 7 and comparative examples A and B were subjected to SDS polyacrylamide gel electrophoresis, which was subsequently stained with Coomassie Blue. A band of approximately 70 kDa, which corresponds to the predicted molecular weight of the LtrA protein was seen in the lanes containing aliquots of the RNP particles of Example 7 and was absent from the lanes containing the RNP particles prepared from comparative examples A and B. On the basis of the Bradford protein assays of the column eluant, the quantity of LtrA protein in RNP particles in the eluant from the chitin column was estimated to be approximately 0.5 mg/liter of start culture. The LtrA protein in these RNP particles was approximately 95% pure. Accordingly, the method of claim 7 is highly preferred for making large amounts of highly purified RNP particles having nucleotide integrase activity.

Using the RNP Particles to Cleave Double-Stranded DNA and to Insert Nucleotide Sequences into the Cleavage Site.

Nucleotide integrases are useful for cleaving RNA substrate, single-stranded DNA substrates and one or both strands of a double-stranded DNA substrate, catalyzing the attachment of the excised, group II intron RNA molecule to the RNA substrate, the single-stranded DNA substrate, and to the first strand, i.e. the strand that contains the IBS1 and IBS2 sequence, of the double-stranded DNA substrate. Nucleotide integrases also catalyze the formation of a cDNA molecule on the second strand, i.e. the strand that is complementary to the first strand, of a cleaved double-stranded DNA substrate. Thus, the nucleotide integrases are useful analytical tools for determining the location of a defined sequence in a double-stranded DNA substrate. Moreover, the simultaneous insertion of the nucleic acid molecule into the first strand of DNA permits tagging of the cleavage site of the first strand with a radiolabeled molecule. In addition, the automatic attachment of an RNA molecule onto one strand of the DNA substrate permits identification of the cleavage site through hybridization studies that use a probe that is complementary to the attached RNA molecule. An attached RNA molecule that is tagged with a molecule such as biotin also enables the cleaved DNA to be affinity purified. Moreover, the cleavage of RNA molecules, single stranded DNA molecules, and one or both strands of a double stranded DNA molecule and the concomitant insertion of a nucleotide sequence into the cleavage site permits incorporation of new genetic information or a genetic marker into the cleavage site, as well as disruption of the cleaved gene. Thus, the nucleotide integrases are also useful for rendering the substrate DNA nonfunctional or for changing the characteristics of the RNA and protein encoded by the substrate DNA.

While RNP particles having nucleotide integrase activity can be used to cleave nucleic acid substrates at a wide range of temperatures, good results are obtained at a reaction temperature from about 30° C. to about 42° C., preferably from about 30° to about 37° C. A suitable reaction medium contains a monovalent cation such as $Na^+$ or $K^+$, and a divalent cation, preferably a magnesium or manganese ion, more preferably a magnesium ion, at a concentration that is less than 100 mM and greater than 1 mM. Preferably the divalent cation is at a concentration of about 5 to about 20 mM. The preferred pH for the medium is from about 6.0–8.5, more preferably about 7.5–8.0.

Because of its reverse transcriptase activity, the LtrA protein, either in the form of an RNP particle which comprises the LtrA protein or as a free protein, i.e., a protein which is not bound to a group II intron RNA, is also useful for transcribing RNA molecules.

Cleavage of Double Stranded DNA Substrates
A. Cleaving a Double-Stranded DNA Substrate with the RNP Particles of Example 1

0.025 $O.D_{260}$ of the RNP particles of Example 1 and comparative examples A and B were incubated for 20 minutes with 150,000 cpm of each of a 5' and 3' end-labeled double-stranded DNA substrate that comprises the wild-type exon 1 and the wild-type exon 2 junction of the ltrB gene. The sequence of the 129 base pair substrate, which comprises the 70 base pair exon 1 and exon 2 junction of the ltrB gene, plus sequences of the plasmid is depicted in FIG. 7A and SEQ. ID. NO. 4. To verify cleavage, the products were isolated on a 6% polyacrylamide gel.

The substrate which is cleaved by the nucleotide integrase, which comprises the excised L1.ltrB intron RNA and the LtrA protein, is schematically depicted in FIG. 8(a). In addition, the IBS1 and IBS2 sequence of the substrate is shown in FIG. 8(b). As shown in FIG. 8, the IBS1 and IBS2 sequences which are complementary to the EBS sequences of the Lltr.B intron RNA are present in exon 1 of the ltrB gene. As depicted in FIG. 8, the RNP particles prepared according to the method of example 1 cleaved the sense strand of the substrate at position 0, which is the exon 1 and exon 2 junction, and cleaved the antisense strand at +9. When the RNP particles prepared according to the method of example 1 were treated with either RNase A/T1 to degrade the RNA in the particles, or with proteinase K to degrade the protein component of the particles prior to incubation of the particles with the substrate, no cleavage of the substrate was observed. These results indicate that both the RNA component and the protein component of the nucleotide integrase are needed to cleave both strands of the substrate DNA.

0.025 $O.D._{260}$ units of the RNP particle preparation of example 1 were reacted with 125 fmoles (150,000 cpm) of the 129 base pair internally-labeled DNA substrate for 20 minutes. To verify cleavage, the products were glyoxalated and analyzed in a 1% agarose gel.

A dark band of radiolabel of approximately 1.0 kb RNA and lighter bands of approximately 0.8, 1.1, 1.4, 1.5, 1.6, 1.9, 2.5, 3.2 were observed on the gel. Pretreatment of the reaction products with RNase prior to separation on the agarose gel resulted in the complete disappearance of these bands. These results indicate that the L1.ltrB intron RNA was attached to the DNA substrate during reaction of the substrate with the RNP particles of example 1. On the basis of the size of L1.trB intron, it is believed that the band at 2.5 kb represents the integration of the full length group II intron RNA into the cleavage site of the sense strand. The presence of smaller radiolabeled products on the gel is believed to be due to degradation of the integrated intron RNA by RNases which may be present during purification. The finding that the RNA-DNA products withstand denaturation with glyoxal indicates a covalent linkage between the intron RNA and the DNA substrate.

B. Cleaving Double-Stranded DNA Substrates using Nucleotide Integrases Prepared by the Methods of Examples 8, 10, and 11.

0.025 $O.D._{260}$ units of the RNP particle preparation of examples 10 and 11 were reacted with 125 fmoles (150,000 cpm) of the 129 base pair internally-labeled DNA substrate for 20 minutes. To verify cleavage, the products were glyoxalated and analyzed in a 1% agarose gel. To verify that the RNA component of the nucleotide integrase had been partially or fully integrated into the cleavage site, sequences of the exon 1 DNA-intron RNA and exon 2 DNA junctions were analyzed by RT-PCR. The RNP particles prepared as described in examples 10 and 11 were able to efficiently cleave the double-stranded DNA substrate and to either partially or fully integrate the intron RNA subunit of the nucleotide integrase into the cleavage site. Thus, RNP particles that comprise LtrA protein and an L1.ltrB intron RNA which lacks an ORF sequence have complete nucleotide integrase activity. Similarly RNP particles that comprise an LtrA protein and an LltrB intron RNA in which the ORF has been replaced with a sequence encoding a different gene product also have complete nucleotide integrase activity 0.025 $O.D._{260}$ units of the RNP particle preparations of example 8 were reacted with 125 fmoles (150,000 cpm) of the 129 base pair internally-labeled double-stranded DNA substrate which comprises the sequence depicted in FIG. 7A for 20 minutes. In addition, 0.025 $O.D._{260}$ units of the RNP particle preparations of example 8 were reacted with 125 fmoles (150,000 cpm) of a 129 base pair internally-labeled double-stranded DNA substrate which comprises a modified exon 1 and wild-type exon 2 of the L1.ltrB gene for 20 minutes. The sequence of the first strand of the 129 base pair substrate, in which the nucleotide at position −6 relative to the putative cleavage site in the wild-type exon 1 is changed from a C to a G is underlined in FIG. 7B. The putative cleavage sites in the first strand of the substrates shown in FIG. 7A and 7B are depicted by a vertical line. To verify cleavage, the products were glyoxalated and analyzed in a 1% agarose gel. Endonuclease assays were also conducted to confirm that cleavage occurred between nucleotides −1 an +1 in the first strand of the substrate and at position +9 in the second strand of the substrate, and also to confirm that a nucleic acid molecule had been inserted into the cleavage site. The RNP particles prepared as described in example 8 were able to efficiently cleave the double-stranded DNA substrate shown in FIG. 7b and to either partially or fully integrate the intron RNA subunit of the RNP particles into the cleavage site. The EBS1 sequence of the modified L1.ltrB intron in the RNP particles prepared as described in example 8 is complementary to the IBS1 sequence of the substrate shown in FIG. 7b. The RNP particles prepared as described in example 8, however, were not able to efficiently cleave the substrate depicted in FIG. 7a. The EBS1 sequence of the modified L1.ltrB intron in the RNP particles prepared as described in example 8 is not complementary to the IBS1 sequence of the substrate shown in FIG. 7a. These results indicate that changing the EBS1 sequence of a group II intron RNA alters the target site specificity of the nucleotide integrase that comprises the modified group II intron RNA.

What is claimed is:

1. A method of preparing RNP particles having nucleotide integrase activity comprising the steps of:
   (a) providing an isolated, excised group II intron RNA;
   (b) providing a group II intron-encoded protein; wherein the group II intron-encoded protein is obtained by a process comprising the following steps:
      (i) introducing a DNA molecule which comprises an open reading frame sequence that encodes said group II intron-encoded protein into a heterologous host cell;
      (ii) expressing said DNA molecule in said host cell to provide a complex comprising said group II intron-encoded protein bound to an RNA molecule;
      (iii) isolating said complex from said host cell; and
      (iv) removing said RNA from said complex to provide said group II intron-encoded protein; and
   (c) then incubating the excised, group II intron RNA with the group II intron-encoded protein to provide an RNP particle comprising the excised, group II intron RNA bound to the group II intron-encoded protein.

2. The method of claim 1 wherein the DNA molecule lacks an intron sequence upstream of said open reading frame sequence.

3. The method of claim 2 wherein said open reading frame sequence is operably linked to a promoter.

4. The method of claim 1 wherein said complex is obtained from a soluble fraction of the host cell.

5. The method of claim 1 wherein the DNA molecule further comprises a nucleotide sequence encoding a tag for facilitating isolation of the complex.

6. The method of claim 5 wherein the nucleotide sequence which encodes the tag is at the 5' end or the 3' end of the open reading frame sequence.

7. The method of claim 1 wherein the RNA is removed from the complex by contacting the complex with a nuclease.

8. The method of claim 1 wherein the isolated, excised, group II intron RNA is a wild-type group II intron RNA.

9. The method of claim 1 wherein the isolated, excised, group II intron RNA is a modified group II intron RNA.

10. The method of claim 9 wherein the modified group II intron RNA comprises a modification in the loop region of domain IV.

11. The method of claim 9 wherein the modified group II intron RNA has a modified EBS1 sequence.

12. The method of claim 9 wherein the modified group II intron RNA has a modified EBS2 sequence.

13. The method of claim 1 wherein said isolated group II intron RNA comprises a first hybridizing sequence capable of hybridizing with a first intron RNA binding sequence on one strand of a DNA substrate and a second hybridizing sequence capable of hybridizing with a second intron RNA binding sequence on said one strand of the DNA substrate.

14. The method of claim 10 wherein said isolated group II intron RNA further comprises a delta nucleotide that is complementary to a delta prime nucleotide on said one strand of the substrate, said delta prime nucleotide being located at position +1 relative to a cleavage site on said one strand of said DNA substrate.

15. A method of preparing RNP particles having nucleotide integrase activity comprising the steps of:
   (a) providing an isolated, excised group II intron RNA;
   (b) providing a group II intron-encoded protein; wherein the group II intron-encoded protein is provided by a process comprising the following steps:
      (i) introducing a DNA molecule which encodes a wild-type or a modified group II intron RNA into a host cell;
      (ii) expressing said DNA molecule to provide a complex comprising said group II intron-encoded protein bound to an RNA molecule;
      (iii) lysing said host cell to provide said complex;
      (iv) isolating said complex from said host cell; and
      (v) removing said RNA from said complex to provide said group II-intron encoded protein; and
   c) then incubating the excised, group II intron RNA with the group II intron-encoded protein to provide an RNP particle comprising the excised, group II intron RNA bound to the group II intron-encoded protein.

16. The method of claim 15 wherein the DNA molecule encodes a splicing-defective group II intron RNA.

17. The method of claim 15 wherein the complex is obtained from a soluble fraction of the lysed cell.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 2761 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

```
AAGCTTAGAG AAAAATAATG CGGTGCTTGG TCATCACCTC ATCCAATCAT TTTCTCCTGA      60

TGACAATCTA ACTCCTGAAC AAATTCATGA AATAGGTCGT CAAACCATAT TAGAATTTAC     120

AGGTGGCGAA TATGAATTTG TGATTGCAAC CCACGTCGAT CGTGAACACA TCCATAACGT     180

GCGCCCAGAT AGGGTGTTAA GTCAAGTAGT TTAAGGTACT ACTCTGTAAG ATAACACAGA     240

AAACAGCCAA CCTAACCGAA AAGCGAAAGC TGATACGGGA ACAGAGCACG GTTGGAAAGC     300

GATGAGTTAC CTAAAGACAA TCGGGTACGA CTGAGTCGCA ATGTTAATCA GATATAAGGT     360

ATAAGTTGTG TTTACTGAAC GCAAGTTTCT AATTTCGGTT ATGTGTCGAT AGAGGAAAGT     420

GTCTGAAACC TCTAGTACAA AGAAAGGTAA GTTATGGTTG TGGACTTATC TGTTATCACC     480

ACATTTGTAC AATCTGTAGG AGAACCTATG GGAACGAAAC GAAAGCGATG CCGAGAATCT     540

GAATTTACCA AGACTTAACA CTAACTGGGG ATACCCTAAA CAAGAATGCC TAATAGAAAG     600

GAGGAAAAAG GCTATAGCAC TAGAGCTTGA AAATCTTGCA AGGGTACGGA GTACTCGTAG     660

TATTCTGAGA AGGGTAACGC CCTTTACATG GCAAAGGGGT ACAGTTATTG TGTACTAAAA     720

TTAAAAATTG ATTAGGGAGG AAAACCTCAA AATGAAACCA ACAATGGCAA TTTTAGAAAG     780

AATCAGTAAA AATTCACAAG AAAATATAGA CGAAGTTTTT ACAAGACTTT ATCGTTATCT     840

TTTACGTCCA GATATTTATT ACGTGGCGTA TCAAAATTTA TATTCCAATA AAGGAGCTTC     900

CACAAAAGGA ATATTAGATG ATACAGCGGA TGGCTTTAGT GAAGAAAAAA TAAAAAAGAT     960

TATTCAATCT TTAAAGACG GAACTTACTA TCCTCAACCT GTACGAAGAA TGTATATTGC    1020

AAAAAAGAAT TCTAAAAAGA TGAGACCTTT AGGAATTCCA ACTTTCACAG ATAAATTGAT    1080

CCAAGAAGCT GTGAGAATAA TTCTTGAATC TATCTATGAA CCGGTATTCG AAGATGTGTC    1140

TCACGGTTTT AGACCTCAAC GAAGCTGTCA CACAGCTTTG AAAACAATCA AAAGAGAGTT    1200

TGGCGGCGCA AGATGGTTTG TGGAGGGAGA TATAAAAGGC TGCTTCGATA ATATAGACCA    1260

CGTTACACTC ATTGGACTCA TCAATCTTAA AATCAAAGAT ATGAAAATGA GCCAATTGAT    1320

TTATAAATTT CTAAAAGCAG GTTATCTGGA AAACTGGCAG TATCACAAAA CTTACAGCGG    1380

AACACCTCAA GGTGGAATTC TATCTCCTCT TTTGGCCAAC ATCTATCTTC ATGAATTGGA    1440

TAAGTTTGTT TTACAACTCA AAATGAAGTT TGACCGAGAA AGTCCAGAAA GAATAACACC    1500

TGAATATCGG GAACTTCACA ATGAGATAAA AAGAATTTCT CACCGTCTCA AGAAGTTGGA    1560

GGGTGAAGAA AAAGCTAAAG TTCTTTTAGA ATATCAAGAA AAACGTAAAA GATTACCCAC    1620
```

-continued

```
ACTCCCCTGT ACCTCACAGA CAAATAAAGT ATTGAAATAC GTCCGGTATG CGGACGACTT      1680

CATTATCTCT GTTAAAGGAA GCAAAGAGGA CTGTCAATGG ATAAAAGAAC AATTAAAACT      1740

TTTTATTCAT AACAAGCTAA AAATGGAATT GAGTGAAGAA AAAACACTCA TCACACATAG      1800

CAGTCAACCC GCTCGTTTTC TGGGATATGA TATACGAGTA AGGAGAAGTG GAACGATAAA      1860

ACGATCTGGT AAAGTCAAAA AGAGAACACT CAATGGGAGT GTAGAACTCC TTATTCCTCT      1920

TCAAGACAAA ATTCGTCAAT TTATTTTTGA CAAGAAAATA GCTATCCAAA AGAAAGATAG      1980

CTCATGGTTT CCAGTTCACA GGAAATATCT TATTCGTTCA ACAGACTTAG AAATCATCAC      2040

AATTTATAAT TCTGAATTAA GAGGGATTTG TAATTACTAC GGTCTAGCAA GTAATTTTAA      2100

CCAGCTCAAT TATTTTGCTT ATCTTATGGA ATACAGCTGT CTAAAAACGA TAGCCTCCAA      2160

ACATAAGGGA ACACTTTCAA AAACCATTTC CATGTTTAAA GATGGAAGTG GTTCGTGGGG      2220

CATCCCGTAT GAGATAAAGC AAGGTAAGCA GCGCCGTTAT TTTGCAAATT TTAGTGAATG      2280

TAAATCCCCT TATCAATTTA CGGATGAGAT AAGTCAAGCT CCTGTATTGT ATGGCTATGC      2340

CCGGAATACT CTTGAAAACA GGTTAAAAGC TAAATGTTGT GAATTATGTG AACATCTGA      2400

TGAAAATACT TCCTATGAAA TTCACCATGT CAATAAGGTC AAAAATCTTA AAGGCAAAGA      2460

AAAATGGGAA ATGGCAATGA TAGCGAAACA ACGTAAAACT CTTGTTGTAT GCTTTCATTG      2520

TCATCGTCAC GTGATTCATA ACACAAGTG AATTTTTACG AACGAACAAT AACAGAGCCG      2580

TATACTCCGA GAGGGTACG TACGGTTCCC GAAGAGGGTG GTGCAAACCA GTCACAGTAA      2640

TGTGAACAAG GCGGTACCTC CCTACTTCAC CATATCATTT TTAATTCTAC GAATCTTTAT      2700

ACTGGCAAAC AATTTGACTG GAAAGTCATT CCTAAAGAGA AACAAAAAG CGGCAAAGCT      2760

T                                                                       2761
```

(2) INFORMATION FOR SEQ ID NO:2:

(i) SEQUENCE CHARACTERISTICS:
        (A) LENGTH: 1800 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..1800

(xi) SEQUENCE DESCRIPTION: SEQ ID NO:2:

```
ATG AAA CCA ACA ATG GCA ATT TTA GAA AGA ATC AGT AAA AAT TCA CAA        48
Met Lys Pro Thr Met Ala Ile Leu Glu Arg Ile Ser Lys Asn Ser Gln
 1               5                  10                  15

GAA AAT ATA GAC GAA GTT TTT ACA AGA CTT TAT CGT TAT CTT TTA CGT        96
Glu Asn Ile Asp Glu Val Phe Thr Arg Leu Tyr Arg Tyr Leu Leu Arg
                20                  25                  30

CCA GAT ATT TAT TAC GTG GCG TAT CAA AAT TTA TAT TCC AAT AAA GGA        144
Pro Asp Ile Tyr Tyr Val Ala Tyr Gln Asn Leu Tyr Ser Asn Lys Gly
            35                  40                  45

GCT TCC ACA AAA GGA ATA TTA GAT GAT ACA GCG GAT GGC TTT AGT GAA        192
Ala Ser Thr Lys Gly Ile Leu Asp Asp Thr Ala Asp Gly Phe Ser Glu
        50                  55                  60

GAA AAA ATA AAA AAG ATT ATT CAA TCT TTA AAA GAC GGA ACT TAC TAT        240
Glu Lys Ile Lys Lys Ile Ile Gln Ser Leu Lys Asp Gly Thr Tyr Tyr
 65                  70                  75                  80

CCT CAA CCT GTA CGA AGA ATG TAT ATT GCA AAA AAG AAT TCT AAA AAG        288
Pro Gln Pro Val Arg Arg Met Tyr Ile Ala Lys Lys Asn Ser Lys Lys
                85                  90                  95
```

| | | |
|---|---|---|
| ATG AGA CCT TTA GGA ATT CCA ACT TTC ACA GAT AAA TTG ATC CAA GAA<br>Met Arg Pro Leu Gly Ile Pro Thr Phe Thr Asp Lys Leu Ile Gln Glu<br>100 105 110 | | 336 |
| GCT GTG AGA ATA ATT CTT GAA TCT ATC TAT GAA CCG GTA TTC GAA GAT<br>Ala Val Arg Ile Ile Leu Glu Ser Ile Tyr Glu Pro Val Phe Glu Asp<br>115 120 125 | | 384 |
| GTG TCT CAC GGT TTT AGA CCT CAA CGA AGC TGT CAC ACA GCT TTG AAA<br>Val Ser His Gly Phe Arg Pro Gln Arg Ser Cys His Thr Ala Leu Lys<br>130 135 140 | | 432 |
| ACA ATC AAA AGA GAG TTT GGC GGC GCA AGA TGG TTT GTG GAG GGA GAT<br>Thr Ile Lys Arg Glu Phe Gly Gly Ala Arg Trp Phe Val Glu Gly Asp<br>145 150 155 160 | | 480 |
| ATA AAA GGC TGC TTC GAT AAT ATA GAC CAC GTT ACA CTC ATT GGA CTC<br>Ile Lys Gly Cys Phe Asp Asn Ile Asp His Val Thr Leu Ile Gly Leu<br>165 170 175 | | 528 |
| ATC AAT CTT AAA ATC AAA GAT ATG AAA ATG AGC CAA TTG ATT TAT AAA<br>Ile Asn Leu Lys Ile Lys Asp Met Lys Met Ser Gln Leu Ile Tyr Lys<br>180 185 190 | | 576 |
| TTT CTA AAA GCA GGT TAT CTG GAA AAC TGG CAG TAT CAC AAA ACT TAC<br>Phe Leu Lys Ala Gly Tyr Leu Glu Asn Trp Gln Tyr His Lys Thr Tyr<br>195 200 205 | | 624 |
| AGC GGA ACA CCT CAA GGT GGA ATT CTA TCT CCT CTT TTG GCC AAC ATC<br>Ser Gly Thr Pro Gln Gly Gly Ile Leu Ser Pro Leu Leu Ala Asn Ile<br>210 215 220 | | 672 |
| TAT CTT CAT GAA TTG GAT AAG TTT GTT TTA CAA CTC AAA ATG AAG TTT<br>Tyr Leu His Glu Leu Asp Lys Phe Val Leu Gln Leu Lys Met Lys Phe<br>225 230 235 240 | | 720 |
| GAC CGA GAA AGT CCA GAA AGA ATA ACA CCT GAA TAT CGG GAA CTT CAC<br>Asp Arg Glu Ser Pro Glu Arg Ile Thr Pro Glu Tyr Arg Glu Leu His<br>245 250 255 | | 768 |
| AAT GAG ATA AAA AGA ATT TCT CAC CGT CTC AAG AAG TTG GAG GGT GAA<br>Asn Glu Ile Lys Arg Ile Ser His Arg Leu Lys Lys Leu Glu Gly Glu<br>260 265 270 | | 816 |
| GAA AAA GCT AAA GTT CTT TTA GAA TAT CAA GAA AAA CGT AAA AGA TTA<br>Glu Lys Ala Lys Val Leu Leu Glu Tyr Gln Glu Lys Arg Lys Arg Leu<br>275 280 285 | | 864 |
| CCC ACA CTC CCC TGT ACC TCA CAG ACA AAT AAA GTA TTG AAA TAC GTC<br>Pro Thr Leu Pro Cys Thr Ser Gln Thr Asn Lys Val Leu Lys Tyr Val<br>290 295 300 | | 912 |
| CGG TAT GCG GAC GAC TTC ATT ATC TCT GTT AAA GGA AGC AAA GAG GAC<br>Arg Tyr Ala Asp Asp Phe Ile Ile Ser Val Lys Gly Ser Lys Glu Asp<br>305 310 315 320 | | 960 |
| TGT CAA TGG ATA AAA GAA CAA TTA AAA CTT TTT ATT CAT AAC AAG CTA<br>Cys Gln Trp Ile Lys Glu Gln Leu Lys Leu Phe Ile His Asn Lys Leu<br>325 330 335 | | 1008 |
| AAA ATG GAA TTG AGT GAA GAA AAA ACA CTC ATC ACA CAT AGC AGT CAA<br>Lys Met Glu Leu Ser Glu Glu Lys Thr Leu Ile Thr His Ser Ser Gln<br>340 345 350 | | 1056 |
| CCC GCT CGT TTT CTG GGA TAT GAT ATA CGA GTA AGG AGA AGT GGA ACG<br>Pro Ala Arg Phe Leu Gly Tyr Asp Ile Arg Val Arg Arg Ser Gly Thr<br>355 360 365 | | 1104 |
| ATA AAA CGA TCT GGT AAA GTC AAA AAG AGA ACA CTC AAT GGG AGT GTA<br>Ile Lys Arg Ser Gly Lys Val Lys Lys Arg Thr Leu Asn Gly Ser Val<br>370 375 380 | | 1152 |
| GAA CTC CTT ATT CCT CTT CAA GAC AAA ATT CGT CAA TTT ATT TTT GAC<br>Glu Leu Leu Ile Pro Leu Gln Asp Lys Ile Arg Gln Phe Ile Phe Asp<br>385 390 395 400 | | 1200 |
| AAG AAA ATA GCT ATC CAA AAG AAA GAT AGC TCA TGG TTT CCA GTT CAC<br>Lys Lys Ile Ala Ile Gln Lys Lys Asp Ser Ser Trp Phe Pro Val His<br>405 410 415 | | 1248 |

```
AGG AAA TAT CTT ATT CGT TCA ACA GAC TTA GAA ATC ATC ACA ATT TAT      1296
Arg Lys Tyr Leu Ile Arg Ser Thr Asp Leu Glu Ile Ile Thr Ile Tyr
            420                 425                 430

AAT TCT GAA TTA AGA GGG ATT TGT AAT TAC TAC GGT CTA GCA AGT AAT      1344
Asn Ser Glu Leu Arg Gly Ile Cys Asn Tyr Tyr Gly Leu Ala Ser Asn
            435                 440                 445

TTT AAC CAG CTC AAT TAT TTT GCT TAT CTT ATG GAA TAC AGC TGT CTA      1392
Phe Asn Gln Leu Asn Tyr Phe Ala Tyr Leu Met Glu Tyr Ser Cys Leu
            450                 455                 460

AAA ACG ATA GCC TCC AAA CAT AAG GGA ACA CTT TCA AAA ACC ATT TCC      1440
Lys Thr Ile Ala Ser Lys His Lys Gly Thr Leu Ser Lys Thr Ile Ser
465                 470                 475                 480

ATG TTT AAA GAT GGA AGT GGT TCG TGG GGC ATC CCG TAT GAG ATA AAG      1488
Met Phe Lys Asp Gly Ser Gly Ser Trp Gly Ile Pro Tyr Glu Ile Lys
            485                 490                 495

CAA GGT AAG CAG CGC CGT TAT TTT GCA AAT TTT AGT GAA TGT AAA TCC      1536
Gln Gly Lys Gln Arg Arg Tyr Phe Ala Asn Phe Ser Glu Cys Lys Ser
            500                 505                 510

CCT TAT CAA TTT ACG GAT GAG ATA AGT CAA GCT CCT GTA TTG TAT GGC      1584
Pro Tyr Gln Phe Thr Asp Glu Ile Ser Gln Ala Pro Val Leu Tyr Gly
            515                 520                 525

TAT GCC CGG AAT ACT CTT GAA AAC AGG TTA AAA GCT AAA TGT TGT GAA      1632
Tyr Ala Arg Asn Thr Leu Glu Asn Arg Leu Lys Ala Lys Cys Cys Glu
            530                 535                 540

TTA TGT GGA ACA TCT GAT GAA AAT ACT TCC TAT GAA ATT CAC CAT GTC      1680
Leu Cys Gly Thr Ser Asp Glu Asn Thr Ser Tyr Glu Ile His His Val
545                 550                 555                 560

AAT AAG GTC AAA AAT CTT AAA GGC AAA GAA AAA TGG GAA ATG GCA ATG      1728
Asn Lys Val Lys Asn Leu Lys Gly Lys Glu Lys Trp Glu Met Ala Met
            565                 570                 575

ATA GCG AAA CAA CGT AAA ACT CTT GTT GTA TGC TTT CAT TGT CAT CGT      1776
Ile Ala Lys Gln Arg Lys Thr Leu Val Val Cys Phe His Cys His Arg
            580                 585                 590

CAC GTG ATT CAT AAA CAC AAG TGA                                      1800
His Val Ile His Lys His Lys  *
            595                 600
```

(2) INFORMATION FOR SEQ ID NO:3:

(i) SEQUENCE CHARACTERISTICS:
        (A) LENGTH: 599 amino acids
        (B) TYPE: amino acid
        (D) TOPOLOGY: linear (ii) MOLECULE TYPE: protein (xi) SEQUENCE DESCRIPTION: SEQ ID NO:3:

```
Met Lys Pro Thr Met Ala Ile Leu Glu Arg Ile Ser Lys Asn Ser Gln
 1               5                  10                  15

Glu Asn Ile Asp Glu Val Phe Thr Arg Leu Tyr Arg Tyr Leu Leu Arg
             20                  25                  30

Pro Asp Ile Tyr Tyr Val Ala Tyr Gln Asn Leu Tyr Ser Asn Lys Gly
         35                  40                  45

Ala Ser Thr Lys Gly Ile Leu Asp Asp Thr Ala Asp Gly Phe Ser Glu
     50                  55                  60

Glu Lys Ile Lys Lys Ile Ile Gln Ser Leu Lys Asp Gly Thr Tyr Tyr
65                  70                  75                  80

Pro Gln Pro Val Arg Arg Met Tyr Ile Ala Lys Lys Asn Ser Lys Lys
             85                  90                  95

Met Arg Pro Leu Gly Ile Pro Thr Phe Thr Asp Lys Leu Ile Gln Glu
```

```
                    100                 105                 110
Ala Val Arg Ile Ile Leu Glu Ser Ile Tyr Glu Pro Val Phe Glu Asp
            115                 120                 125
Val Ser His Gly Phe Arg Pro Gln Arg Ser Cys His Thr Ala Leu Lys
130                 135                 140
Thr Ile Lys Arg Glu Phe Gly Gly Ala Arg Trp Phe Val Glu Gly Asp
145                 150                 155                 160
Ile Lys Gly Cys Phe Asp Asn Ile Asp His Val Thr Leu Ile Gly Leu
                165                 170                 175
Ile Asn Leu Lys Ile Lys Asp Met Lys Met Ser Gln Leu Ile Tyr Lys
            180                 185                 190
Phe Leu Lys Ala Gly Tyr Leu Glu Asn Trp Gln Tyr His Lys Thr Tyr
            195                 200                 205
Ser Gly Thr Pro Gln Gly Gly Ile Leu Ser Pro Leu Leu Ala Asn Ile
210                 215                 220
Tyr Leu His Glu Leu Asp Lys Phe Val Leu Gln Leu Lys Met Lys Phe
225                 230                 235                 240
Asp Arg Glu Ser Pro Glu Arg Ile Thr Pro Glu Tyr Arg Glu Leu His
                245                 250                 255
Asn Glu Ile Lys Arg Ile Ser His Arg Leu Lys Lys Leu Glu Gly Glu
            260                 265                 270
Glu Lys Ala Lys Val Leu Leu Glu Tyr Gln Glu Lys Arg Lys Arg Leu
            275                 280                 285
Pro Thr Leu Pro Cys Thr Ser Gln Thr Asn Lys Val Leu Lys Tyr Val
            290                 295                 300
Arg Tyr Ala Asp Asp Phe Ile Ile Ser Val Lys Gly Ser Lys Glu Asp
305                 310                 315                 320
Cys Gln Trp Ile Lys Glu Gln Leu Lys Leu Phe Ile His Asn Lys Leu
                325                 330                 335
Lys Met Glu Leu Ser Glu Glu Lys Thr Leu Ile Thr His Ser Ser Gln
            340                 345                 350
Pro Ala Arg Phe Leu Gly Tyr Asp Ile Arg Val Arg Arg Ser Gly Thr
            355                 360                 365
Ile Lys Arg Ser Gly Lys Val Lys Lys Arg Thr Leu Asn Gly Ser Val
            370                 375                 380
Glu Leu Leu Ile Pro Leu Gln Asp Lys Ile Arg Gln Phe Ile Phe Asp
385                 390                 395                 400
Lys Lys Ile Ala Ile Gln Lys Lys Asp Ser Ser Trp Phe Pro Val His
                405                 410                 415
Arg Lys Tyr Leu Ile Arg Ser Thr Asp Leu Glu Ile Ile Thr Ile Tyr
                420                 425                 430
Asn Ser Glu Leu Arg Gly Ile Cys Asn Tyr Tyr Gly Leu Ala Ser Asn
            435                 440                 445
Phe Asn Gln Leu Asn Tyr Phe Ala Tyr Leu Met Glu Tyr Ser Cys Leu
            450                 455                 460
Lys Thr Ile Ala Ser Lys His Lys Gly Thr Leu Ser Lys Thr Ile Ser
465                 470                 475                 480
Met Phe Lys Asp Gly Ser Gly Ser Trp Gly Ile Pro Tyr Glu Ile Lys
                485                 490                 495
Gln Gly Lys Gln Arg Arg Tyr Phe Ala Asn Phe Ser Glu Cys Lys Ser
            500                 505                 510
Pro Tyr Gln Phe Thr Asp Glu Ile Ser Gln Ala Pro Val Leu Tyr Gly
            515                 520                 525
```

```
Tyr Ala Arg Asn Thr Leu Glu Asn Arg Leu Lys Ala Lys Cys Cys Glu
    530                 535                 540
Leu Cys Gly Thr Ser Asp Glu Asn Thr Ser Tyr Glu Ile His His Val
545                 550                 555                 560
Asn Lys Val Lys Asn Leu Lys Gly Lys Glu Lys Trp Glu Met Ala Met
                565                 570                 575
Ile Ala Lys Gln Arg Lys Thr Leu Val Val Cys Phe His Cys His Arg
            580                 585                 590
His Val Ile His Lys His Lys
        595
```

(2) INFORMATION FOR SEQ ID NO:4:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CGCTCTAGAA CTAGTGGATC CTTGCAACCC ACGTCGATCG TGAACACATC CATAACCATA      60
TCATTTTTAA TTCTACGAAT CTTTATACTG GGAATTCGAT ATCAAGCTTA TCGATACCGT     120
CGACCTCGA                                                             129
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
TCACCTCATC TAGACATTTT CTCC                                             24
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

```
CGTTCGTAAA GCTAGCCTTG TGTTTATG                                         28
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CACAAAGTGA TCATTTAACG AACG                                             24
```

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TTGGGATCCT CATAAGCTTT GCCGC                                             25

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CAAAGGATCC GATGAAACCA ACAATGGCAA                                        30

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGTGGCTTCC ATATGCTTGG TCATCACCTC ATC                                    33

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGTAGAACCA TATGAAATTC CTCCTCCCTA ATCAATTTT                              39

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

AAACCTCCAT ATGAAACCAA CAATG                                             25

(2) INFORMATION FOR SEQ ID NO:13:

(i) SEQUENCE CHARACTERISTICS:
        (A) LENGTH: 24 base pairs
        (B) TYPE: nucleic acid (C) STRANDEDNESS: double
        (D) TOPOLOGY: linear (ii) MOLECULE TYPE: DNA (genomic)

(xi) SEQUENCE DESCRIPTION: SEQ ID NO:13:

TCGATCGTGA ACACATCCAT AACC                                              24

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

TAACTTCCCG GGCTTGTGTT TATGAATCAC                                        30

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

GGATCGAGAT CTCGATCCCG                                                   20

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

CGCACGTTAT CGATGTGTTC AC                                                22

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

TTATGGTTGT CGACTTATCT GTTATC                                            26

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

CTTCGAATAC CGGTTCATAG                                              20

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

GGGGGGGCTA GCACGCGTCG CCACGTAATA AATATCTGGA CG                     42

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

GGGGGGGCTA GCACGCGTTG GGAAATGGCA ATGATAGC                          38

(2) INFORMATION FOR SEQ ID NO:21:

(i) SEQUENCE CHARACTERISTICS:
        (A) LENGTH:  129 base pairs
        (B) TYPE:  nucleic acid
        (C) STRANDEDNESS:  double
        (D) TOPOLOGY:  linear (ii) MOLECULE TYPE: DNA (xi) SEQUENCE DESCRIPTION:  SEQ ID NO:21:

CGCTCTAGAA CTAGTGGATC CTTGCAACCC ACGTCGATCG TGAACACATC CATAACCATA   60

TCATTTTTAA TTCTACGAAT CTTTATACTG GGAATTCGAT ATCAAGCTTA TCGATACCGT  120

CGACCTCGA                                                         129

(2) INFORMATION FOR SEQ ID NO:22:

(i) SEQUENCE CHARACTERISTICS:
        (A) LENGTH:   129 base pairs
        (B) TYPE:  nucleic acid
        (C) STRANDEDNESS:  double
        (D) TOPOLOGY: linear (ii) MOLECULE TYPE:  DNA (xi) SEQUENCE DESCRIPTION:  SEQ ID NO:22:

CGCTCTAGAA CTAGTGGATC CTTGCAACCC ACGTCGATCG TGAACACATC GATAACCATA   60

TCATTTTTAA TTCTACGAAT CTTTATACTG GGAATTCGAT ATCAAGCTTA TCGATACCGT  120

CGACCTCGA                                                         129

(2) INFORMATION FOR SEQ ID NO:23:

(i) SEQUENCE CHARACTERISTICS:
        (A) LENGTH:   53 base pairs
        (B) TYPE:  nucleic acid
        (C) STRANDEDNESS:  double
        (D) TOPOLOGY:  linear -continued (ii) MOLECULE TYPE: DNA (xi) SEQUENCE DESCRIPTION: SEQ ID NO:23:

AACCCACGTC GATCGTGAAC ACATCCATAA CCATATCATT TTTAATTCTA CGA    53